(12) United States Patent
Faustman

(10) Patent No.: US 12,174,188 B2
(45) Date of Patent: Dec. 24, 2024

(54) METHODS OF IDENTIFYING SUBJECTS RESPONSIVE TO TREATMENT FOR TYPE 1 DIABETES AND COMPOSITIONS FOR TREATING THE SAME

(71) Applicant: The General Hospital Corporation, Boston, MA (US)

(72) Inventor: Denise L. Faustman, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/027,757

(22) PCT Filed: Oct. 16, 2014

(86) PCT No.: PCT/US2014/060908
§ 371 (c)(1),
(2) Date: Apr. 7, 2016

(87) PCT Pub. No.: WO2015/057968
PCT Pub. Date: Apr. 23, 2015

(65) Prior Publication Data
US 2016/0245808 A1 Aug. 25, 2016

Related U.S. Application Data

(60) Provisional application No. 61/892,140, filed on Oct. 17, 2013.

(51) Int. Cl.
| | |
|---|---|
| G01N 33/566 | (2006.01) |
| A61K 39/04 | (2006.01) |
| A61K 45/06 | (2006.01) |
| G01N 33/50 | (2006.01) |
| G01N 33/564 | (2006.01) |
| A61K 39/00 | (2006.01) |

(52) U.S. Cl.
CPC ........... *G01N 33/566* (2013.01); *A61K 39/04* (2013.01); *A61K 45/06* (2013.01); *G01N 33/505* (2013.01); *G01N 33/564* (2013.01); *A61K 2039/572* (2013.01); *G01N 2333/47* (2013.01); *G01N 2333/62* (2013.01); *G01N 2333/70517* (2013.01); *G01N 2800/042* (2013.01); *G01N 2800/24* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,309,418 A | 1/1982 | Green |
| 4,457,916 A | 7/1984 | Hayashi et al. |
| 4,495,282 A | 1/1985 | Ohnishi et al. |
| 4,677,063 A | 6/1987 | Mark et al. |
| 4,677,064 A | 6/1987 | Mark et al. |
| 4,681,760 A | 7/1987 | Fathman |
| 4,791,101 A | 12/1988 | Adolf |
| 4,816,567 A | 3/1989 | Cabilly et al. |
| 4,879,226 A | 11/1989 | Wallace et al. |
| 4,963,354 A | 10/1990 | Shepard et al. |
| 4,985,241 A | 1/1991 | Zimmerman et al. |
| 5,002,876 A | 3/1991 | Sreekrishna et al. |
| 5,059,530 A | 10/1991 | Oshima et al. |
| 5,139,481 A | 8/1992 | Faustman et al. |
| 5,166,142 A | 11/1992 | Moss et al. |
| 5,215,743 A | 6/1993 | Singh et al. |
| 5,283,058 A | 2/1994 | Faustman |
| 5,288,852 A | 2/1994 | Yamada et al. |
| 5,370,870 A | 12/1994 | Wong |
| 5,487,984 A | 1/1996 | Allet et al. |
| 5,538,854 A | 7/1996 | Faustman |
| 5,560,908 A | 10/1996 | Satoh et al. |

(Continued)

FOREIGN PATENT DOCUMENTS

| | | |
|---|---|---|
| EP | 0612529 A2 | 8/1994 |
| EP | 2295588 A1 | 3/2011 |

(Continued)

OTHER PUBLICATIONS

Jones, A.G. and Hattersley, A.T. Diabetic Med. 2013;30:803-817.*
Molinaro, R. Diabetes. Am. Assoc. Clin. Med. 2013: slides 1-60.*
Koskinen, P.J., et al. Diabetes Care;11(4):318-322 (Year: 1988).*
Abraham et al., "Human pancreatic islet-derived progenitor cell engraftment in immunocompetent mice," Am J Pathol. 164(3):817-30 (2004).
Al-Awqati et al., "Stem cells in the kidney," Kidney Int. 61(2):387-95 (2002).
Aldrich et al., "Positive selection of self- and alloreactive CD8+ T cells in Tap-1 mutant mice," Proc Natl Acad Sci USA. 91(14):6525-8 (1994).

(Continued)

*Primary Examiner* — Sharon X Wen
(74) *Attorney, Agent, or Firm* — Clark & Elbing LLP

(57) ABSTRACT

The invention features methods of identifying a subject having an autoimmune disease, such as type 1 diabetes, as likely to respond to treatment with a tumor necrosis factor-α (TNF-α) receptor II activator. The method involves measuring CD8 protein density on the surface of autoreactive $CD8^+$ T cells and identifying the subject as likely to respond to the treatment if the CD8 protein density is reduced relative to a reference $CD8^+$ T cell. For type 1 diabetes, the method may involve measuring C-peptide levels in an in vitro biological sample from the subject, identifying the subject as likely to respond to the treatment if the C-peptide levels are detectable, and identifying the subject as unlikely to respond to the treatment if the C-peptide are substantially undetectable. The invention also features pharmaceutical compositions of one or more TNFR2 activators for use in treating an autoimmune disease in a subject identified as likely to respond to the treatment prior to the treating by according to the methods of the invention.

8 Claims, 4 Drawing Sheets

Specification includes a Sequence Listing.

(56) References Cited

U.S. PATENT DOCUMENTS

| | | | |
|---|---|---|---|
| 5,593,698 | A | 1/1997 | Weiner et al. |
| 5,783,216 | A | 7/1998 | Faustman |
| 5,821,337 | A | 10/1998 | Carter et al. |
| 5,843,425 | A | 12/1998 | Sachs et al. |
| 5,843,452 | A | 12/1998 | Wiedmann et al. |
| 5,874,306 | A | 2/1999 | Beattie et al. |
| 5,919,452 | A | 7/1999 | Le et al. |
| 6,046,031 | A | 4/2000 | Ni et al. |
| 6,056,952 | A | 5/2000 | Rosenberg |
| 6,110,206 | A | 8/2000 | Stone |
| 6,159,461 | A | 12/2000 | Besmer et al. |
| 6,165,737 | A | 12/2000 | Wang et al. |
| 6,177,076 | B1 | 1/2001 | Lattime et al. |
| 6,284,879 | B1 | 9/2001 | Faustman |
| 6,414,218 | B1 | 7/2002 | Faustman et al. |
| 6,420,139 | B1 | 7/2002 | Classen |
| 6,491,908 | B1 | 12/2002 | Rosenberg |
| 6,599,710 | B1 | 7/2003 | Faustman |
| 6,617,171 | B2 | 9/2003 | Faustman et al. |
| 6,660,487 | B2 | 12/2003 | Faustman |
| 6,773,705 | B1 | 8/2004 | Faustman et al. |
| 6,844,011 | B1 | 1/2005 | Faustman |
| 6,866,843 | B2 | 3/2005 | Habener et al. |
| 6,923,959 | B2 | 8/2005 | Habener et al. |
| 6,984,380 | B1 | 1/2006 | Faustman |
| 7,015,037 | B1 | 3/2006 | Furcht et al. |
| 7,438,902 | B2 | 10/2008 | Habener et al. |
| 7,485,293 | B1 | 2/2009 | Faustman |
| 7,510,877 | B2 | 3/2009 | Yilmaz et al. |
| 7,537,756 | B2 | 5/2009 | Habener et al. |
| 7,582,313 | B2 | 9/2009 | Faustman |
| 7,628,988 | B2 | 12/2009 | Faustman |
| RE41,887 | E | 10/2010 | Faustman |
| 7,867,765 | B2 | 1/2011 | Faustman et al. |
| 8,017,392 | B2 | 9/2011 | Faustman |
| 8,021,693 | B2 | 9/2011 | Faustman |
| 8,173,129 | B2 | 5/2012 | Faustman |
| 8,187,886 | B2 | 5/2012 | Faustman et al. |
| RE43,467 | E | 6/2012 | Faustman |
| 8,697,077 | B2 | 4/2014 | Faustman |
| 8,753,888 | B2 | 6/2014 | Faustman et al. |
| 8,969,015 | B2 | 3/2015 | Faustman |
| 9,410,144 | B2 | 8/2016 | Faustman et al. |
| 9,522,181 | B2 | 12/2016 | Faustman |
| 2002/0106689 | A1 | 8/2002 | Faustman et al. |
| 2002/0123472 | A1 | 9/2002 | Faustman |
| 2002/0187548 | A1 | 12/2002 | Keller et al. |
| 2003/0005469 | A1 | 1/2003 | Faustman et al. |
| 2003/0031657 | A1 | 2/2003 | Habener et al. |
| 2004/0028658 | A1 | 2/2004 | Faustman |
| 2004/0031066 | A9 | 2/2004 | Faustman et al. |
| 2004/0229785 | A1 | 11/2004 | Faustman |
| 2004/0235160 | A1 | 11/2004 | Nishikawa et al. |
| 2005/0080239 | A1 | 4/2005 | Ditzel et al. |
| 2005/0158288 | A1 | 7/2005 | Faustman |
| 2005/0158302 | A1 | 7/2005 | Faustman et al. |
| 2005/0181502 | A1 | 8/2005 | Furcht et al. |
| 2005/0244386 | A1 | 11/2005 | Habener et al. |
| 2006/0062769 | A1 | 3/2006 | Habener et al. |
| 2006/0069161 | A1 | 3/2006 | Lee et al. |
| 2006/0292155 | A1 | 12/2006 | Golz et al. |
| 2007/0116688 | A1 | 5/2007 | Faustman |
| 2007/0135338 | A1 | 6/2007 | O'Neil et al. |
| 2007/0238649 | A1 | 10/2007 | Kadowaki et al. |
| 2008/0102054 | A1 | 5/2008 | Faustman |
| 2008/0175830 | A1 | 7/2008 | Steinman et al. |
| 2008/0233149 | A1 | 9/2008 | Mittelman et al. |
| 2009/0054358 | A1 | 2/2009 | Small et al. |
| 2009/0257982 | A1 | 10/2009 | Scheiber et al. |
| 2010/0068177 | A1 | 3/2010 | Faustman |
| 2010/0151062 | A1 | 6/2010 | Stefanon |
| 2010/0183727 | A1 | 7/2010 | Lannacone et al. |
| 2010/0298232 | A1 | 11/2010 | Liu |
| 2011/0111476 | A1 | 5/2011 | Faustman et al. |
| 2011/0177051 | A1 | 7/2011 | Galski-Lorberboum et al. |
| 2011/0177592 | A1 | 7/2011 | Faustman et al. |
| 2012/0045435 | A1 | 2/2012 | Deisher |
| 2012/0196919 | A1 | 8/2012 | Brown et al. |
| 2012/0201856 | A1 | 8/2012 | Marchal et al. |
| 2012/0295246 | A1 | 11/2012 | Faustman et al. |
| 2013/0115207 | A1 | 5/2013 | Faustman |
| 2013/0230850 | A1 | 9/2013 | Akirav |
| 2014/0134644 | A1 | 5/2014 | Faustman |
| 2014/0186400 | A1 | 7/2014 | Faustman |
| 2014/0369973 | A1 | 12/2014 | Bernstein et al. |
| 2015/0038816 | A1 | 2/2015 | Tokita et al. |
| 2015/0111276 | A1 | 4/2015 | Faustman et al. |
| 2015/0322424 | A1 | 11/2015 | Faustman et al. |
| 2015/0366909 | A1 | 12/2015 | Faustman |
| 2016/0245808 | A1 | 8/2016 | Faustman |
| 2018/0296658 | A1 | 10/2018 | Faustman |

FOREIGN PATENT DOCUMENTS

| | | |
|---|---|---|
| EP | 2446818 A1 | 5/2012 |
| JP | 2013-534925 A | 9/2013 |
| WO | WO-92/04033 A1 | 3/1992 |
| WO | WO-93/02690 A1 | 2/1993 |
| WO | WO-94/09137 A1 | 4/1994 |
| WO | WO-95/24914 A1 | 9/1995 |
| WO | WO-95/25533 A1 | 9/1995 |
| WO | WO-97/08328 A1 | 3/1997 |
| WO | WO-97/21802 A1 | 6/1997 |
| WO | WO-99/53953 A2 | 10/1999 |
| WO | WO-99/59632 A1 | 11/1999 |
| WO | WO-00/53209 A1 | 9/2000 |
| WO | WO-02/26819 A2 | 4/2002 |
| WO | WO-2004/003164 A2 | 1/2004 |
| WO | WO-2005/042727 A2 | 5/2005 |
| WO | WO-2006/109044 A2 | 10/2006 |
| WO | WO-2011163566 A2 | 12/2011 |
| WO | WO-2012/122464 A1 | 9/2012 |
| WO | WO-2012/174522 A1 | 12/2012 |
| WO | WO-2014/124134 A1 | 8/2014 |
| WO | WO-2014/186311 A1 | 11/2014 |
| WO | WO-2015/057968 A2 | 4/2015 |

OTHER PUBLICATIONS

Allen et al., "Effect of bacillus Calmette-Guerin vaccination on new-onset Type 1 Diabetes," Diabetes Care. 22(10):1703-1707 (1999).

Altomonte et al., "Serum levels of interleukin-1b, tumour necrosis factor-a and interleukin-2 in rheumatoid arthritis. Correlation with disease activity," Clin Rheumatol. 11(2):202-205 (1992).

Anderson et al., "Can stem cells cross lineage boundaries?," Nat Med. 7(4):393-5 (2001).

Anderson et al., "The NOD mouse: a model of immune dysregulation," Annu Rev Immunol. 23:447-485 (2005).

Aranda et al., "Analysis of intestinal lymphocytes in mouse colitis mediated by transfer of CD4+, CD45RBhigh T Cells to SCID recipients," J Immunol. 158(7):3464-3473 (1997).

Aristarkhov et al., "E2-C, a cyclin-selective ubiquitin carrier protein required for the destruction of mitotic cyclins," Proc Natl Acad Sci USA. 93(9):4294-9 (1996).

Ashton-Rickardt et al., "Evidence for a differential avidity model of T Cell selection in the thymus," Cell. 76(4):651-63 (1994).

Ashton-Rickardt et al., "Peptide contributes to the specificity of positive selection of CD8+ T Cells in the thymus," Cell. 73(5):1041-9 (1993).

Atkinson et al., "The NOD mouse model of Type 1 Diabetes: As good as it gets?," Nat Med. 5(6):601-604 (1999).

Baeuerle et al., "NF-kappaB: Ten years after," Cell. 87(1):13-20 (1996).

Baeza et al., "Reg protein: a potential beta-cell-specific growth factor?," Diabetes Metab. 22(4):229-234 (1996).

Baeza et al., "Specific reg II gene overexpression in the non-obese diabetic mouse pancreas during active diabetogenesis," FEBS Letters. 416(3):364-8 (1997).

(56) References Cited

OTHER PUBLICATIONS

Baik et al., "BCG vaccine prevents insulitis in low dose streptozotocin-induced diabetic mice," Diabetes Res Clin Pract. 46(2):91-97 (1999).
Baldwin, "The NF-$_{kappa}$B and I$_{kappa}$B proteins: new discoveries and insights," Ann Rev Immunol. 14:649-683 (1996).
Ban et al., "Selective death of autoreactive T Cells in human diabetes by TNF or TNF receptor 2 agonism," Proc Natl Acad Sci USA 105(36):13644-13649 (2008).
Barres, "A new role for glia: generation of neurons!," Cell. 97(6): 667-70 (1999).
Baxter et al., "Mycobacteria precipitate an SLE-like syndrome in diabetes-prone NOD mice," Immunology. 83(2):227-231 (1994).
Beers et al. Disorders of Carbohydrate Metabolism: Diabetes Mellitus. *The Merck Manual of Diagnosis and Therapy, 17th Ed.* Merck Research Laboratories, 165-171, 1999.
Beg et al., "An essential role for NF-kappaB in preventing TNF-alpha-induced cell death," Science. 274(5288):782-784 (1996).
Bendelac et al., "Syngeneic transfer of autoimmune diabetes from diabetic NOD mice to healthy neonates," J Exp Med. 166(4):823-832 (1987).
Benkler et al., "Parkinson's disease, autoimmunity, and olfaction," Int J Neurosci. 119(12):2133-43 (2009) (Abstract only) (1 page).
Bercovici et al., "Systemic administration of agonist peptide blocks the progression of spontaneous CD8-mediated autoimmune diabetes in transgenic mice without bystander damage," J Immunol. 165(1):202-10 (2000).
Bill et al, "Use of soluble MHC class II/peptide multimers to detect antigen-specific T cells in human disease," Arthritis Res. 4:261-265 (2002).
Bjornson et al., "Turning brain into blood: A hematopoietic fate adopted by adult neural stem cells vitro," Science. 283:534-537 (1999).
Bleumink et al., "Etanercept-induced subacute cutaneous lupus erythematosus" Rheumatology. 40:1317-1319 (2001).
Boches et al, "Role for the adenosine triphosphate-dependent proteolytic pathway in reticulocyte maturation," Science. 215:978-980 (1982).
Brazelton et al., "From marrow to brain: expression of neuronal phenotypes in adult mice," Science. 290:1775-1779 (2000).
Brod et al., "Ingested interferon alpha suppresses Type I diabetes in non-obese diabetic mice," Diabetologia. 41:1227-1232 (1998).
Brodbeck et al., "Genetic determination of nephrogenesis: the Pax/Eya/Six gene network," Pediatr Nephrol. 19(3):249-255 (2004) (Abstract Only).
Brás et al., "Diabetes-prone NOD mice are resistant to mycobacterium avium and the infection prevents autoimmune disease," Immunology. 89:20-25 (1996).
Bunting et al., "Enforced P-glycoprotein pump function in murine bone marrow cells results in expansion of side population stem cells in vitro and repopulating cells in vivo," Blood. 96(3):902-909 (2000).
Burger et al., "Novel automated blood separations validate whole cell biomarkers," PLoS One. 6(7):e22430 (2011) (11 pages).
Burnham et al., "Oral BCG vaccine in Crohn's disease," Gut. 20:229-233 (1979).
Caetano et al., "Effect of methotrexate (MTX) on NAD(P)+ dehydrogenases of Hela cells: malic enzyme, 2-oxoglutarate and isocitrate dehydrogenases," Cell Biochem Funct. 15(4):259-264 (1997).
Cairns et al., "New onset systemic lupus erythematosus in a patient receiving etanercept for rheumatoid arthritis," Ann Rheum Dis. 61(11):1031-2 (2002).
Cavallo et al., "BCG vaccine with and without nicotinamide in recent onset IDDM: a multicenter randomized trial," Second Congress of the Immunology of Diabetes Society. 18, A063 (1996).
Cebrián et al., "MHC-I expression renders catecholaminergic neurons susceptible to T-cell-mediated degeneration," Nat Commun. 5:3633 (2014) (Abstract only) (1 page).
Charles et al., "Assessment of antibodies to double-stranded DNA induced in rheumatoid arthritis patients following treatment with infliximab, a monoclonal antibody to tumor necrosis factor alpha: findings in open-label and randomized placebo-controlled trials." Arthritis Rheum. 43(11):2383-90 (2000).
Chatenoud et al., "CD3 antibody-induced dominant self tolerance in overtly diabetic NOD mice," J Immunol. 158(6):2947-2954 (1997).
Choi et al., "Prevention of Encephalomyocarditis virus-induced diabetes by live recombinant *Mycobacterium bovis* Bacillus Calmette-Guérin in susceptible mice," Diabetes. 49:1459-1467 (2000).
Chopra et al., "Exogenous TNFR2 activation protects from acute GvHD via host T reg cell expansion", J Exp Med 213(9):1881-1900 (2016) (21 pages).
Christen et al., "A dual role for TNF-alpha in type 1 diabetes: islet-specific expression abrogates the ongoing autoimmune process when induced late but not early during pathogenesis," J Immunol. 166(12):7023-32 (2001).
Cole et al., "Two ParaHox genes, SpLox and SpCdx, interact to partition the posterior endoderm in the formation of a functional gut," Development. 136(4):541-549 (2009).
Colucci et al., "Programmed cell death in the pathogenesis of murine IDDM: resistance to apoptosis induced in lymphocytes by cyclophosphamide," J Autoimmunity 9:271-276 (1996).
Corbett et al., "Nitric oxide mediates cytokine-induced inhibition of insulin secretion by human islets of langerhans," Proc Natl Acad Sci USA. 90(5):1731-1735 (1993).
Coux et al., "Enzymes catalyzing ubiquitination and proteolytic processing of the p105 precursor of nuclear factor kappaB1," J Biol Chem. 273(15):8820-8828 (1998).
Couzin, "Diabetes studies conflict on power of spleen cells," Science. 311:1694 (2006).
Creasey et al., "Biological effects of recombinant human tumor necrosis factor and its novel muteins on tumor and normal cell lines," Cancer Res. 47(1):145-9 (1987).
D'Andrea, "Add Alzheimer's disease to the list of autoimmune diseases," Med Hypotheses. 64(3):458-63 (2005) (Abstract only) (2 pages).
Dale et al., "A role for transcription factor NF-kappaB in autoimmunity: possible interactions of genes, sex, and the immune response," Adv Physiol Educ. 30(4):152-8 (2006).
Darzynkiewicz et al., "Use of flow and laser scanning cytometry to study mechanisms regulating cell cycle and controlling cell death," Clinics in Laboratory Medicine. 21(4):857-873 (2001).
Dear et al., "The Hox11 gene is essential for cell survival during spleen development," Development. 121:2909-2915 (1995).
Dieguez-Acuna et al., "Characterization of mouse spleen cells by subtractive proteomics," Mol Cell Proteomics. 4(10):1459-1470 (2005).
Dieguez-Acuña et al., "Proteomics identifies multipotent and low oncogenic risk stem cells of the spleen," Int J Biochem Cell Biol. 42(10):1651-1660 (2009) (10 pages).
Dieguez-Acuña et al., "Proteomics identifies multipotent and low oncogenic risk stem cells of the spleen," Int J Biochem Cell Biol. 42(10):1651-1660 (2010). keep.
Dilts et al., "Autoimmune diabetes: The involvement of benign and malignant autoimmunity," J Autoimmun. 12:229-232 (1999).
Dinarello, "Interleukin-1, Interleukin-1 receptors and Interleukin-1 receptor antagonist," Intern Rev Immunol. 16:457-499 (1998).
Driscoll et al., "The proteasome (multicatalytic protease) is a component of the 1500-kDa proteolytic complex which degrades ubiquitin-conjugated proteins," J Biol Chem. 265(9):4789- 4792 (1990).
Durand et al., "Mesenchymal lineage potentials of aorta-gonad-mesonephros stromal clones," Heamatologica. 91(9):1172-1179 (2006).
Eglitis et al., "Hematopoietic cells differentiate into both microglia and macroglia in the brains of adult mice," Proc Natl Acad Sci USA. 94:4080-4085 (1997).
Elliott et al., "Effect of Bacille Calmette-Guérin vaccination on C-Peptide secretion in children newly diagnosed with IDDM," Diabetes Care. 21(10):1691-1693 (1998).
Enayati et al., "Association of anti-tumor necrosis factor therapy with the development of multiple sclerosis," J Clin Gastroenterol. 39(4): 303-6 (2005) (Abstract only).
"The Hippo signaling pathway is required for salivary gland development and its dysregulation is associated with Sjogren's-like

(56) References Cited

OTHER PUBLICATIONS disease," available in PMC May 1, 2014, published in vinal edited form as: Lab Invest. 93(11):1203-18 (2013) (27 pages).
Engleman et al., "Treatment of NZB/NZW F1 hybrid mice with *Mycobacterium bovis* strain BCG or type II interferon preparations accelerates autoimmune disease," Arthritis Rheum. 24(11):1396-1402 (1981).
Eytan et al., "ATP-dependent incorporation of 20S protease into the 26S complex that degrades proteins conjugated to ubiquitin," Proc Natl Acad Sci USA. 86:7751-7755 (1989).
Fan et al., "Generation of p50 subunit of NF-kappaB by processing of p105 through an ATP-dependent pathway," Nature. 354:395-398 (1991).
Faustman et al., "Cells for repair: breakout session summary," Ann N Y Acad Sci. 961:45-7 (2002).
Faustman et al., "Comment on papers by Chong et al., Nishio et al., and Suri et al. on diabetes reversal in NOD mice," Science. 314(5803):1243 (2006) (2 pages).
Faustman et al., "Murine pancreatic beta-Cells express H-2K and H-2D but not Ia antigens," J Exp Med. 151:1563-1568 (1980).
Faustman et al., "Prevention of xenograft rejection by masking donor HLA class I antigens," Science. 252:1700-1702 (1991).
Faustman et al., "Proof-of-concept, randomized, controlled clinical trial of Bacillus-Calmette-Guerin for treatment of long-term type 1 diabetes," PLoS One. 7(8):e41756 (2012) (16 pages).
Faustman et al., "Reversal of Sjogren's-like syndrome in non-obese diabetic mice," Science 314(5803):1243 (2006).
Faustman et al., "The primacy of CD8 T lymphocytes in type 1 diabetes and implications for therapies," J Mol Med (Berl). 87(12):1173-8 (2009) (6 pages).
Faustman et al., "TNF Receptor 2 and Disease: Autoimmunity and Regenerative Medicine," Front Immunol. 4:478 (2013) (8 pages).
Faustman et al., "TNF receptor 2 pathway: drug target for autoimmune diseases," Nat Rev Drug Discov. 9(6):482-93 (2010).
Faustman et al., "Treatment of primary Sjögren syndrome with rituximab," Ann Intern Med. 161(5):376-80 (2014).
"EBV infection and anti-CD3 treatment for Type 1 diabetes: bad cop, good cop?" available in PMC Jul. 2, 2014, published in final edited form as: Expert Rev Clin Immunol. 9(2):95-7 (2013) (4 pages).
Faustman, "Immunotherapy on trial for new-onset type 1 diabetes," N Engl J Med. 359(18):1956-8 (2008).
Faustman, "Permanent reversal of diabetes in NOD mice," Science. 317(5835):196 (2007).
Faustman, "Reversal of established autoimmune diabetes by in situ beta-cell regeneration," Ann N Y Acad Sci. 961:40 (2002).
Faustman, "Reversal of type 1 diabetes in mice," N Engl J Med. 356(3):311-2 (2007).
Faustman, "Why were we wrong for so long? The pancreas of type 1 diabetic patients commonly functions for decades," Diabetologia. 57(1):1-3 (2014).
Feldman et al., "Anti-TNFalpha therapy is useful in rheumatoid arthritis and Crohn's disease: Analysis of the mechanism of action predicts utility in other diseases," Transplant Proc. 30(8):4126-4127 (1998).
Feldman et al., "Role of cytokines in rheumatoid arthritis," Annu Rev Immunol. 14:397-440 (1996) (abstract only).
Ferrando et al., "Adult T-Cell ALL patients whose lymphoblasts express the HOX11 oncogene have an excellent prognosis when treated with chemotherapy and are not candidates for allogeneic bone marrow transplantation in first remission," Blood. 11:Abstract 578 (2002).
Fischer et al., "A Tnf receptor 2 selective agonist rescues human neurons from oxidative stress-induced cell death," PloS One. 6(11):e27621(1-11) (2011).
Fischer et al., "An improved flow cytometric assay for the determination of cytotoxic T lymphocyte activity," J Immunol Methods. 259:159-169 (2002).
Foulis, "C.L. Oakley lecture (1987). The pathogenesis of beta cell destruction in Type I (insulin-dependent) diabetes mellitus," J Pathol. 152(3):141-148 (1987).
Fu et al., "Antigen processing and autoimmunity: Evaluation of mRNA abundance and function of HLA-Linked genes," Ann NY Acad Sci. 842:138-155 (1998).
Fu et al., "Defective major histocompatibility complex class I expression on lymphoid cells in autoimmunity," J Clin Invest. 91:2301-2307 (1993).
Faustman, "Regenerative medicine: Stem cell research turns to the spleen," Discov Med. 5(29):447-9 (2005).
Fukada et al., "Two signals are necessary for cell proliferation induced by a cytokine receptor gp130: Involvement of STAT3 in anti-apoptosis," Immunity. 5:449-460 (1996).
Gage et al., "Multipotent progenitor cells in the adult dentate gyrus," J Neurobiol. 36:249-266 (1998).
Gage, "Mammalian neural stem cells," Science. 287:1433-1438 (2000).
Galaria et al., "Leukocytoclastic vasculitis due to etanercept," J Rheumatol. 27(8):2041-4 (2000) (Abstract only).
Ganoth et al., "A multicomponent system that degrades proteins conjugated to ubiquitin. Resolution of factors and evidence for ATP-dependent complex formation," J Biol Chem. 263(25):12412-12419 (1988).
Gaur et al., "Induction of islet allotolerance in nonhuman primates," Ann NY Acad Sci. 958:199-203 (2002).
Gazda et al., "Regulation of autoimmune diabetes: characteristics of non-islet-antigen specific therapies," Immunol Cell Biol. 74: 401-407 (1996).
Genestier et al., "Immunosuppressive properties of methotrexate: Apoptosis and clonal deletion of activated peripheral T Cells," J Clin Invest. 102(2):322-328 (1998).
Gerich et al., "Advances in diabetes for the millenium: Understanding insulin resistance," MedGenMed. 6(3 Suppl): 11:1-9 (2004).
Ghosh et al., "Activation in vitro of NF-kappaB by phosphorylation of its inhibitor IkappaB," Nature. 344:678-682 (1990).
Glas et al., "The CD8+ T Cell repertoire in beta2-microglobulin-deficient mice is biased towards reactivity against self-major histocompatibility class I," J Exp Med. 179(2):661-672 (1994).
Goldberg, "Functions of the proteasome: The lysis at the end of the tunnel," Science. 268:522-523 (1995).
Goldberg, "The mechanism and functions of ATP-dependent proteases in bacterial and animal cells," Eur J Biochem. 203:9-23 (1992).
Gottlieb et al., "Cell acidification in apoptosis: Granulocyte colony-stimulating factor delays programmed cell death in neutrophils by up-regulating the vacuolar H+-ATPase," Proc Natl Acad Sci USA. 92:5965-5968 (1995).
Graves et al., "Lack of association between early childhood immunizations and beta-Cell autoimmunity," Diabetes Care 22:1694-1697 (1999).
Grewal et al., "Local expression of transgene encoded TNFalpha in islets prevents autoimmune diabetes in nonobese diabetic (NOD) mice by preventing the development of auto-reactive islet-specific T Cells," J Exp Med. 184:1963-1974 (1996).
Grilli et al., "Neuroprotection by aspirin and sodium salicylate through blockade of NF-kappaB activation," Science. 274:1383-1385 (1996).
Gronostajski et al., "The ATP dependence of the degradation of short- and long-lived proteins in growing fibroblasts," J Biol Chem. 260(6):3344-3349 (1985).
Gueckel et al., "Mutations in the yeast proteasome beta-Type subunit Pre3 uncover position-dependent effects on proteasomal peptidase activity and in vivo function," J Biol Chem. 273(31):19443-19452 (1998).
Gupta, "Molecular steps of tumor necrosis factor receptor-mediated apoptosis," Curr Mol Med. 1(3):317-324 (2001).
Haas et al., "Pathways of ubiquitin conjugation," FASEB J. 11:1257-1268 (1997).
Hao et al., "Effect of mycophenolate mofetil on islet allografting to chemically induced or spontaneously diabetic animals," Transplant Proc. 24(6): 2843-2844 (1992).

(56) References Cited

OTHER PUBLICATIONS

Harada et al., "Prevention of overt diabetes and insulitis in NOD mice by a single BCG vaccination," Diabetes Res Clin Pract. 8:85-89 (1990).
Hartwell et al., "Aberrant cytokine regulation in macrophages from young autoimmune-prone mice: Evidence that the intrinsic defect in MRL macrophage IL-1 expression is transcriptionally controlled," Mol Immunol. 32(10):743-751 (1995).
Hayashi et al., "Development of spontaneous uterine tumors in low molecular mass polypeptide-2 knockout mice," Cancer Res. 62(1):24-7 (2002).
Hayashi et al., "Essential role of human leukocyte antigen-encoded proteasome subunits in NF-kappaB activation and prevention of tumor necrosis factor-alpha-induced apoptosis," J Biol Chem. 275(7):5238-5247 (2000).
Hayashi et al., "NOD mice are defective in proteasome production and activation of NF-kappaB," Mol Cell Biol. 19(12):8646-8659 (1999).
Hayashi et al., "Role of defective apoptosis in type 1 diabetes and other autoimmune diseases," Recent Prog Horm Res. 58:131-53 (2003).
Hershko et al., "The ubiquitin system for protein degradation," Annu Rev Biochem. 61: 761-807 (1992).
Hester et al., "Studies on the cytophilic properties of human beta2-microglobulin. II. The role of histocompatibility antigens," Scand J Immunol. 9(2):125-134 (1979).
Hoffmann et al. "Large-scale in vitro expansion of polyclonal human CD4(+)CD25high regulatory cells," Blood. 104(3):895-903 (2004).
Horsfall et al., "Characterization and specificity of B-cell responses in lupus induced by *Mycobacterium bovis* in NOD/Lt mice," Immunology 95:8-17 (1998).
Horwitz et al., "Recombinant baccillus Calmette-Guérin (BCG) vaccines expressing the *Mycobacterium tuberculosis* 30-kDa major secretory protein induce greater protective immunity against tuberculosis than conventional BCG vaccines in a highly susceptible animal model," Proc Natl Acad Sci USA. 97(35):13853-13858 (2000).
Hostikka et al., "The mouse Hoxc11 gene: genomic structure and expression pattern," Mech Dev. 70(1-2):133-145 (1998) (Abstract Only).
Hsu et al., "TRADD-TRAF2 and TRADD-FADD interactions define two distinct TNF receptor 1 signal transduction pathways," Cell. 84:299-308 (1996).
Humphreys-Behr et al., "New concepts for the development of autoimmune exocrinopathy derived from studies with the NOD mouse model," Arch Oral Biol. 44(Suppl 1):S21-S25 (1999) (Abstract Only).
Hyafil et al., "Dissociation and exchange of the beta2-micoglobulin subunit of HLA-A and HLA-B antigens," Proc Natl Acad Sci USA. 76(11):5834-5838 (1979).
Hymowitz et al., "Toward small-molecule agonists of TNF receptors," Nat Chem Biol. 1(7):353-354 (2005).
Jacob et al., "Monoclonal anti-tumor necrosis factor antibody renders non-obese diabetic mice hypersensitive to irradiation and enhances insulitis development," Int Immunol. 4(5):611-614 (1992).
Jacob et al., "Prevention of diabetes in nonobese diabetic mice by tumor necrosis factor (TNF): Similarities between TNF-alpha and interleukin 1," Proc Natl Acad Sci USA. 87:968-972 (1990).
Jacob et al., "Tumour necrosis factor-aplha in murine autoimmune 'lupus' nephritis," Nature. 331:356-358 (1988).
Jakubowski et al., "Phase I trial of intramuscularly administered tumor necrosis factor in patients with advanced cancer," J Clin Oncol. 7(3):298-303 (1989).
Jarrett et al., "Anti-tumor necrosis factor-alpha therapy-induced vasculitis: case series," J Rheumatol. 30(10):2287-91 (2003) (Absract only).
Jiang et al., "Pluripotency of mesenchymal stem cells derived from adult marrow," Nature. 418:41-49 (2002).
Johansson et al., "Identification of a neural stem cell in the adult mammalian central nervous system," Cell. 96:25-34 (1999).
Kaijzel et al., "Functional analysis of a human tumor necrosis factor alpha (TNF-alpha) promoter polymorphism related to joint damage in rheumatoid arthritis," Mol Med. 4:724-733 (1998).
Kanzler et al., "Hox11 acts cell autonomously in spleen development and its absence results in altered cell fate of mesenchymal spleen precursors," Devel Biol. 234:231-243 (2001).
Kaufman et al., "Patterns of hemopoietic reconstitution in nonobese diabetic mice: dichotomy of allogeneic resistance versus competitive advantage of disease-resistant marrow," J Immunol. 158(5):2435-2442 (1997).
Kawasaki et al., "Prevention of type 1 diabetes: from the view point of beta cell damage," Diabetes Res Clin Pract. 66:S27-S32 (2004).
Kieran et al., "The DNA binding subunit of NF-kappaB is identical to factor KBF1 and homologous to the rel oncogene product," Cell. 62:1007-1018 (1990).
Klingensmith et al., "Vaccination with BCG at diagnosis does not alter the course of IDDM," Diabetes 57th Annual Meeting and Scientific Sessions, Jun. 21-24, Boston MA. 40(Suppl 1):193A, 0744 (1997) (3 pages).
Klinkhoff, "Biological agents for rheumatoid arthritis: targeting both physical function and structural damage," Drugs. 64(12):1267-83 (2004) (Abstract only).
Koarada et al., "B Cells lacking RP105, A novel B cell antigen, in systemic lupus erythematosus," Arthritis & Rheumatism. 42(12):2593-2600 (1999).
Kodama et al., "Diabetes and stem cell researchers turn to the lowly spleen," Sci Aging Knowledge Environ. 2005(3)pe2 (2005).
Kodama et al., "Islet regeneration during the reversal of autoimmune diabetes in NOD mice," Science. 302:1223-1227 (2003).
Kodama et al., "Regenerative medicine: A radical reappraisal of the spleen," Trends Mol Med. 11(6):271-276 (2005).
Kodama et al., "Routes to regenerating islet cells: stem cells and other biological therapies for type 1 diabetes," Pediatr Diabetes. 5(Suppl 2):38-44 (2004).
Kodama et al., "The therapeutic potential of tumor necrosis factor for autoimmune disease: A mechanically based hypothesis," Cell Mol Life Sci. 62:1850-1862 (2005).
Kopp and Ghosh, "Inhibition of NF-KB by sodium salicylate and aspirin," Science. 265:956-959 (1994).
Kopp et al., "Inhibition of NF-kappaB by sodium salicylate and aspirin," Science. 265:956-959 (1994).
Kouskoff et al., "Organ-specific disease provoked by systemic autoimmunity," Cell. 87(5):811-822 (1996) (Abstract Only).
Koyama et al., "Hox11 genes establish synovial joint organization and phylogenetic characteristics in developing mouse zeugopod skeletal elements," Development. 137(22): 3795800 (2010 (Abstract Only).
Krause et al., "Multi-organ, multi-lineage engraftment by a single bone marrow-derived stem cell," Cell. 105:369-377 (2001).
Kuehnle and Goodell, "The therapeutic potential of stem cells from adults," BMJ. 325:372-376 (2002).
Kuehnle et al., "The therapeutic potential of stem cells from adults," BMJ. 325:372-376 (2002).
Kwon et al., "Evidence for involvement of the proteasome complex (26S) and NFkappaB in IL-1 beta-induced nitric oxide and prostaglandin production by rat islets and RINm5F Cells" Diabetes. 47:583-591 (1998).
Kwon et al., "Interleukin-1beta-induced nitric oxide synthase expression by rat pancreatic beta-cells: Evidence for the involvement of nuclear factor kappaB in the signaling mechanism," Endocrinology. 136(11):4790-4795 (1995).
Kühtreiber et al., "Methods to characterize lymphoid apoptosis in a murine model of autoreactivity," J Immunol Methods. 306(1-2):137-50 (2005).
Laakko et al., "Versatility of merocyanine 540 for the flow cytometric detection of apoptosis in human and murine cells," J Immunol Methods. 261:129-139 (2002).
Lahav-Baratz et al., "Reversible phosphorylation controls the activity of cyclosome-associated cyclin-ubiquitin ligase," Proc Natl Acad Sci USA 92:9303-9307 (1995).

(56) References Cited

OTHER PUBLICATIONS

Lakey et al., "BCG immunotherapy prevents recurrence of diabetes in islet grafts transplanted into spontaneously diabetic NOD mice," Transplantation. 57(8):1213-1217 (1994).
Lammert et al., "Induction of pancreatic differentiation by signals from blood vessels," Science. 294:564-567 (2001).
Lanza et al., "Transplantation of encapsulated canine islets into spontaneously diabetic BB/Wor rats without immunosuppression," Endocrinology. 131(2):637-642 (1992).
Lapchak et al., "Tumor necrosis factor production is deficient in diabetes-prone BB rats and can be corrected by complete Freund's adjuvant: A possible immunoregulatory role of tumor necrosis factor in the prevention of diabetes," Clin Immunol Immunopathol. 65(2):129-134 (1992).
Lawrence et al., "Differential hepatocyte toxicity of recombinant Apo2L/TRAIL versions," Nat Med. 7(4):383-385 (2001).
Lewis et al., "Integrins regulate the apoptotic response to DNA damage through modulation of p53," Proc Natl Acad Sci USA. 99(6):3627-3632 (2002).
Li and Faustman, "Use of Donor β2-Microglobulin-Deficient Transgenic Mouse Liver Cells for Isografts, Allografts, and Xenografts," *Transplantation* 55:940-946, 1993.
Li et al., "Abnormal class I assembly and peptide presentation in the nonobese diabetic mouse," Proc Natl Acad Sci USA. 91:11128-11132 (1994).
Li et al., "Reduced expression of peptide-loaded HLA class I molecules on multiple sclerosis lymphocytes," Ann Neurol. 38:147-154 (1995).
Li et al., "Use of Donor beta2-Microglobulin-Deficient Transgenic Mouse Liver Cells for Isografts, Allografts, and Xenografts," *Transplantation*. 55(4):940-946, 1993.
Lipsky et al., "Infliximab and methotrexate in the treatment of rheumatoid arthritis," N Eng J Med. 343:1594-1602 (2000).
Ljunggren et al., "MHC class I expression and CD8+ T cell development in TAP1/beta2-microglobulin double mutant mice," Int Immunol. 7(6):975-984 (1995).
Loetscher et al., "Human tumor necrosis factor alpha (TNF alpha) mutants with exclusive specificity for the 55-kDa or 75-kDa TNF receptors," J Biol Chem. 268(35):26350-26357 (1993).
"Fetal Hox11 expression patterns predict defective target organs: a novel link between developmental biology and autoimmunity," available in PMC Jul. 30, 2014, published in final edited form as: Immunol Cell Biol. 86(4):301-9 (2008) (19 pages).
Macchi et al., "Impaired apoptosis in mitogen-stimulated lymphocytes of patients with multiple sclerosis," NeuroReport. 10(25):399-402 (1999).
Mak et al., "Signaling for survival and apoptosis in the immune system," Arthritis Res. 4(Suppl 3):S243-S252 (2002).
Markiewicz et al., "Long-term T cell memory requires the surface expression of self-peptide/major histocompatibility complex molecules," Proc Natl Sci USA. 95:3065-3070 (1998).
Marriott, "TNF-alpha antagonists: Monoclonal antibodies, soluble receptors, thalidomide and other novel approaches," Expert Opin Invest Drugs. 6(8):1105-1108 (1997).
Martinez-Gamboa et al., "Gene expression of catalytic proteasome subunits and resistance toward proteasome inhibition of B lymphocytes from patients with primary sjogren syndrome," J Rheumatol. 40(5):663-73 (2013).
Matsumoto et al., "Liver organogenesis promoted by endothelial cells prior to vascular function," Science. 294:559-563 (2001).
Mayer-Proschel et al., "Isolation of lineage-restricted neuronal precursors from multipotent neuroepithelial stem cells," Neuron. 19:773-785 (1997).
McGuire et al., "An enzyme related to the high molecular weight multicatalytic proteinases, macropain, participates in a ubiquitin-mediated, ATP-stimulated proteolytic pathway in soluble extracts of Bhk 21/C13 fibroblasts," Biochim Biophys Acta. 967:195-203 (1988).
McKay, "Mammalian deconstruction for stem cell reconstruction," Nat Med. 6(7):747-748 (2000).

Mera et al., "The spleen contributes stem cells to peripheral blood stem cell transplants," J Stem Cell Res Ther. 4(11):1000253 (2014) (4 pages).
Mercurio et al., "p105 and p98 precursor proteins play an active role in NF-Kappa B-mediated signal transduction," Genes Dev. 7:705-718 (1993).
Mestas et al., "Of mice and not men: Differences between mouse and human immunology," J Immunol. 172:2731-2738 (2004).
Mezey et al., "Turning blood into brain: Cells bearing neuronal antigens generated in vivo from bone marrow," Science. 290: 1779-1782 (2000).
Mittleman et al., "A phase I pharmacokinetic study of recombinant human tumor necrosis factor administered by a 5-day continuous infusion," Invest New Drugs. 10(3):183-190 (1992).
Miyazaki et al., "Predominance of T lymphocytes in pancreatic islets and spleen of pre-diabetic non-obese diabetic (NOD) mice: A longitudinal study," Clin Exp Immunol. 60:622-630 (1985).
Morawietz et al., "Expression of proteasomal immunosubunit beta1i is dysregulated in inflammatory infiltrates of minor salivary glands in Sjogren's syndrome," J Rheumatol. 36(12):2694-703 (2009).
Moreland et al., "Etanercept therapy in rheumatoid arthritis: a randomized, controlled trial," Ann Intern Med. 130(6):478-486 (1999).
Morrison, "Stem cell potential: Can anything make anything?" Curr Biol. 11:R7-R9 (2001).
Munshi et al., "Use of serum c-peptide level to simplify diabetes treatment regimens in older adults," Am J Med. 122(4):395-7 (2009).
Nomikos et al., "Combined treatment with nicotinamide and desferrioxamine prevents islet allograft destruction in NOD mice," Diabetes. 35:1302-1304 (1986).
Offield et al., "PDX-1 is required for pancreatic outgrowth and differentiation of the rostral duodenum," Development. 122:983-995 (1996).
Okubo et al., "Homogeneous expansion of human T-regulatory cells via tumor necrosis factor receptor 2," Sci Rep. 3:3153 (2013) (11 pages).
Okubo et al., "Treg activation defect in type 1 diabetes: correction with TNFR2 agonism," Clin Transl Immunology. 8:5(1):e56 (2016) (9 pages).
Ono et al., "IDDM in BB rats. Enhanced MHC Class I heavy-chain gene expression in pancreatic islets," Diabetes. 37:1411-1418 (1988).
Orlowski, "The multicatalytic proteinase complex, a major extralysosomal proteolytic system," Biochemistry. 29(45):10289-10297 (1990).
Osorio et al., "Beta-2 microglobulin gene disruption prolongs murine islet allograft survival in NOD mice," Transplant Proc. 26(2):752 (1994).
Palombella et al., "The ubiquitin-proteasome pathway is required for processing the NF-$_{kappa}$B1 precursor protein and the activation of NF-*kappa*B," Cell. 78:773-785 (1994).
Paolillo et al., "The effect of bacille calmette-guérin on the evolution of new enhancing lesions to hypointense T1 lesions in relapsing remitting MS," J Neurol. 250:247-248 (2003).
Penfornis et al., "Analysis of TAP2 polymorphisms in Finnish individuals with type I diabetes," Hum Immunol. 63(1):61-70 (2002).
Penfornis et al., "Polymorphisms of human TAP2 detected by denaturing gradient gel electrophoresis," Hum Immunol. 64(1):156-67 (2003).
Pestano et al., "Inactivation of misselected CD8 T cells by CD8 gene methylation and cell death," Science. 284:1187-1191 (1999).
Pozzilli, "BCG vaccine in insulin-dependent diabetes mellitus," Lancet. 349:1520-1521 (1997).
Prieto et al., "Apoptotic rate: A new indicator for the quantification of the incidence of apoptosis in cell cultures," Cytometry. 48:185-193 (2002).
Qin et al., "BCG vaccination prevents insulin-dependent diabetes mellitus (IDDM) in NOD mice after disease acceleration with cyclophosphamide," J Autoimmun. 10:271-278 (1997).
Qin et al., "Complete Freund's adjuvant-induced T cells prevent the development and adoptive transfer of diabetes in nonobese diabetic mice," J Immunol. 150:2072-2080 (1993).

(56) References Cited

OTHER PUBLICATIONS

Quintana et al., "Experimental autoimmune myasthenia gravis in naïve non-obese diabetic (NOD/LtJ) mice: Susceptibility associated with natural IgG antibodies to the acetylcholine receptor," Int Immunol. 15(1):11-16 (2003).
Raab et al., "In vitro evaluation of methotrexate and azathioprine for antipsoriatic activity," Arch Derm Res. 253:77-84 (1975).
Rabinovitch et al., "TNF-alpha down-regulates type 1 cytokines and prolongs survival of syngeneic islet grafts in nonobese diabetic mice," J Immunol. 159:6298-6303 (1997).
Rabinovitch et al., "Tumor necrosis factor mediates the protective effect of freund's adjuvant against autoimmune diabetes in BB rats," J Autoimmun. 8:357-366 (1995).
Rajagopalan et al., "Pathogenic anti-DNA autoantibody-inducing T helper cell lines from patients with active lupus nephritis: Isolation of CD4-8- T helper cell lines that express the gamma delta T-cell antigen receptor," Proc Natl Acad Sci USA. 87:7020-7024 (1990).
Raju et al., "Characterization and developmental expression of Tlx-1, the murine homolog of HOX11," Mech Dev. 44:51-64 (1993).
Ramiya et al., "Reversal of insulin-dependent diabetes using islets generated in vitro from pancreatic stem cells," Nat Med. 6(3):278-282 (2000).
Rath et al., "TNF-induced signaling in apoptosis," J Clin Immunol. 19(6):350-364 (1999).
Rechsteiner, "Ubiquitin-mediated pathways for intracellular proteolysis," Annu Rev Cell Biol. 3:1-30 (1987).
Rietze et al., "Purification of a pluripotent neural stem cell from the adult mouse brain," Nature. 412:736-739 (2001).
Ristori et al., "Use of Bacille Calmette-Guerin (BCG) in multiple sclerosis," Neurology. 53:1588-1589 (1999).
Roberts et al., "Developmental expression of Hox11 and specification of splenic cell fate," Am J Pathol. 146(5):1089-1101 (1995).
Roberts et al., "Hox11 controls the genesis of the spleen," Nature. 368:747-749 (1994).
Robertson et al., "Preservation of insulin mRNA levels and insulin secretion in HIT cells by avoidance of chronic exposure to high glucose concentrations," J Clin Invest. 90:320-325 (1992).
Robinson et al., "A novel NOD-derived murine model of primary Sjögren's Syndrome," Arth Rheum. 41(1):150-156 (1998).
Robinson et al., "Elevated levels of cysteine protease activity in saliva and salivary glands of the nonobese diabetic (NOD) mouse model for Sjögren Syndrome," Proc Natl Acad Sci USA. 94:5767-5771 (1997).
Rolfe et al., "The ubiquitin-mediated proteolytic pathway as a therapeutic area," J Mol Med. 75:5-17 (1997).
Rosenthal, "Prometheus's vulture and the stem-cell promise," N Engl J Med. 349:267-274 (2003).
Ryu et al., "Reversal of established autoimmune diabetes by restoration of endogenous beta cell function," J Clin Invest. 108:63-72 (2001).
Sadelain et al., "Prevention of type I diabetes in NOD mice by adjuvant immunotherapy," Diabetes. 39:583-589 (1990).
Sandborn et al., "Antitumor necrosis factor therapy for inflammatory bowel disease: a review of agents, pharmacology, clinical results, and safety," Inflamm Bowel Dis. 5(2):119-33 (1999) (Abstract only).
Sandborn, "Strategies targeting tumor necrosis factor in Crohn's disease," Acta Gastroenterol Belg. 64(2):170-2 (2001) (Abstract only).
Sarin et al., "Cytotoxic effect of TNF and lymphotoxin on T lymphoblasts," J Immunol. 155:3716-3718 (1995).
Satoh et al., "Inhibition of type I diabetes in BB rats with recombinant human tumor necrosis factor-alpha," J Immunol. 145(5):1395-1399 (1990).
Satoh et al., "Recombinant human tumor necrosis factor alpha suppresses autoimmune diabetes in non obese diabetic mice," J Clin Invest. 84:1345-1348 (1989).
Schatz et al., "Defective inducer T-cell function before the onset of insulin-dependent diabetes mellitus," J Autoimmun. 4:125-136 (1991).

Schmidt et al., "Interspecies exchange of beta2-microglobulin and associated MHC and differentiation antigens," Immunogenetics. 13(6):483-49 (1981).
Schuppan, "Current concepts of Celiac Disease pathogenesis," Gastroenterology. 119:234-242 (2000).
Sears et al., "NF-kappaB p105 processing via the ubiquitin-proteasome pathway," J Biol Chem. 273(3):1409-1419 (1998).
Serrano et al., "Non-HLA associations with autoimmune diseases," Autoimmun Rev. 5:209-214 (2006).
Serreze et al., "Th1 to Th2 cytokine shifts in nonobese diabetic mice: Sometimes an outcome, rather than the cause, of diabetes resistance elicited by immunostimulation," J Immunol. 166:1352-1359 (2001).
Serup et al., "Islet and stem cell transplantation for treating diabetes," BMJ. 322:29-32 (2001).
Serup, "Panning for pancreatic stem cells," Nat Genet. 25:134-135 (2000).
Shehadeh et al., "Effect of adjuvant therapy on development of diabetes in mouse and man," Lancet. 343:706-707 (1994).
Shehadeh et al., "Repeated BCG vaccination is more effective than a single dose in preventing diabetes in non-obese diabetic (NOD) mice," Isr J Med Sci. 33(11):711-715 (1997).
Shihabuddin et al., "Adult spinal cord stem cells generate neurons after transplantation in the adult dentate gyrus," J Neurosci. 20(23):8727-8735 (2000).
Shohami et al., "Dual role of tumor necrosis factor alpha in brain injury," Cytokine Growth Factor Rev. 10:119-130 (1999).
Silva et al., "Prevention of autoimmune diabetes through immunostimulation with Q fever complement-fixing antigen," Ann NY Acad Sci. 1005:423-430 (2003).
Singh et al., "Can progression of IDDM be prevented in newly diagnosed patients by BCG immunotherapy?" Diabetes Metab Rev. 13(4):320-321 (1997).
Slack, "Stem cells in epithelial tissues," Science. 287:1431-1433 (2000).
Song et al., "Tumor necrosis factor-related apoptosis-inducing ligand (TRAIL) is an inhibitor of autoimmune inflammation and cell cycle progression," J Exp Med. 191(7):1095-1103 (2000).
Speiser et al., "Loss of ATP-dependent proteolysis with maturation of reticulocytes and erythrocytes," J Biol Chem. 257(23):14122-14127 (1982).
Sreenan et al., "Increased beta-Cell proliferation and reduced mass before diabetes onset in the nonobese diabetic mouse," Diabetes. 48:989-996 (1999).
Stephens et al., "Protection of NIT-1 pancreatic beta-cells from immune attack by inhibition of NF-kappaB," J Autoimmun. 10:293-298 (1997).
Storms et al., "Hoechst dye efflux reveals a novel CD7+CD34-lymphoid progenitor in human umbilical cord blood," Blood. 96(6):2125-2133 (2000).
Sun et al., "MHC class I multimers," Arthritis Res. 3(5):265-269 (2001).
Swale et al., "Etanercept-induced systemic lupus erythematosus," Clin Exp Dermatol. 28:604-607 (2003).
Swirski et al., "Identification of splenic reservoir monocytes and their deployment to inflammatory sites," Science. 325(5940):612-616 (2009) (12 pages).
Szodoray et al., "Programmed cell death in rheumatoid arthritis peripheral blood T-cell subpopulations determined by laser scanning cytometry," Lab Invest. 83(12):1839-1848 (2003).
Tartaglia et al, "The two different receptors for tumor necrosis factor mediate distinct cellular responses," Proc Natl Acad Sci USA. 88:9292-9296 (1991).
Tavernier et al., "Analysis of the structure-function relationship of tumour necrosis factor. Human/mouse chimeric TNF proteins: general properties and epitope analysis," J Mol Biol. 211(2):493-501 (1990).
Technical Data Sheet for Purified Rat Anti-Human CD120b, BD Pharmingen™ (2011) (2 pages).
Thomas et al., "Demyelination during anti-tumor necrosis factor alpha therapy with infliximab for Crohn's disease," Inflamm Bowel Dis. 10(1):28-31 (2004) (Abstract only).

(56) References Cited

OTHER PUBLICATIONS

Toma et al., "Isolation of multipotent adult stem cells from the dermis of mammalian skin," Nat Cell Bio. 3:778-784 (2001).
Totpal et al., "TNF and its receptor antibody agonist differ in mediation of cellular responses," J Immunol. 153:2248-2257 (1994).
Townsley et al., "Dominant-negative cyclin-selective ubiquitin carrier protein E2-C/UbcH10 blocks cells in metaphase," Proc Natl Acad Sci USA. 94:2362-2367 (1997).
Tran et al., "Reversal of Sjögren's-like syndrome in non-obese diabetic mice," Ann Rheum Dis. 66:812-814 (2007).
Trowsdale et al., "Sequences encoded in the class II region of the MHC related to the 'ABC' superfamily of transporters," Nature. 348:741-744 (1990).
Ulaeto et al., "A T-cell dormant state in the autoimmune process of nonobese diabetic mice treated with complete Freund's adjuvant," Proc Natl Acad Sci USA. 89:3927-3931 (1992).
Van der Kooy et al., "Why stem cells?," Science. 287:1439-1441 (2000).
Van Nocker et al., "The multiubiquitin-chain-binding protein Mcb1 is a component of the 26S proteasome in *Saccharomyces cerevisiae* and plays a nonessential, substrate-specific role in protein turnover," Mol Cell Biol. 16(11):6020-6028 (1996).
Van Noort et al., "Cell biology of autoimmune diseases," Int Rev Cytol. 178:127-204 (1998).
Van Zee et al., "A human tumor necrosis factor (TNF) alpha mutant that binds exclusively to the p55 TNF receptor produces toxicity in the baboon," J Exp Med. 179(4):1185-1191 (1994).
Vidal-Puig et al., "Tolerance to peripheral tissue Is transient and maintained by tissue-specific class I expression," Transplant Proc. 26:3314-3316 (1994).
Vogel, "Stem cell research. Studies cast doubt on plasticity of adult cells," Science. 295:1989, 1991 (2002).
Vogel, "Studies cast doubt on plasticity of adult cells," Science. 295:1989&1991 (2002).
Von Herrath et al., "In vivo treatment with a MHC class I-restricted blocking peptide can prevent virus-induced autoimmune diabetes," J Immunol. 161:5087-5096 (1998).
Wang et al., "Persistence of prolonged C-peptide production in type 1 diabetes as measured with an ultrasensitive C-peptide assay," Diabetes Care. 35(3):465-70 (2012).
Wang et al., "Prevention of recurrence of IDDM in islet-transplanted diabetic NOD mice by adjuvant immunotherapy," Diabetes. 41:114-117 (1992).
Watt et al., "Out of eden: stem cells and their niches," Science. 287:1427-1430 (2000).
Waxman et al., "Demonstration of two distinct high molecular weight proteases in rabbit reticulocytes, one of which degrades ubiquitin conjugates," J Biol Chem. 262(6):2451-2457 (1987).
Weissman, "Translating stem and progenitor cell biology to the clinic: barriers and opportunities," Science. 287:1442-1446 (2000).
Welborn et al., "A human tumor necrosis factor p75 receptor agonist stimulates in vitro T cell proliferation but does not produce inflammation or shock in the baboon," J Exp Med. 184(1):165- 171 (1996).
Wellik et al., "Hox11 paralogous genes are essential for metanephric kidney induction," Genes Dev. 16:1423-1432 (2002).
Weringer et al., "Identification of T cell subsets and Class I and Class II antigen expression in islet grafts and pancreatic islets of diabetic BioBreeding/Worcester rats," Am J Pathol. 132(2):292-303 (1988).
Willis et al., "Type 1 Diabetes in insulin-treated adult-onset diabetic subjects," Diabetes Res Clin Pract. 42:49-53 (1998).
Wilson et al., "Bone-marrow haematopoietic-stem-cell niches," Nat Rev Immunol. 6(2):93-106 (2006).
Winston, "Embryonic stem cell research: the case for . . . ," Nat Med. 7(4):396-397 (2001).
Wong et al., "Identification of an MHC class I-restricted autoantigen in Type I Diabetes by screening an organ-specific cDNA library," Nat Med. 5(9):1026-1031 (1999).
Xu et al., "MHC/peptide tetramer-based studies of T cell function," J Immunol Methods. 268:21-28 (2002).
Yagi et al., "Possible mechanism of the preventive effect of BCG against diabetes mellitus in NOD Mouse. I. Generation of suppressor macrophages in spleen cells of BCG-vaccinated mice," Cell Immunol. 138:130-141 (1991).
Yagi et al., "Possible mechanism of the preventive effect of BCG against diabetes mellitus in NOD Mouse. II. Suppression of pathogenesis by macrophage transfer from BCG-vaccinated mice," Cell Immunol. 138:142-149 (1991).
Yan et al., "Impaired processing and presentation by MHC class II proteins in human diabetic cells," J Immunol. 170(1):620-7 (2003).
Yan et al., "Reduced expression of Tap1 and Lmp2 antigen-processing genes in the nonobese diabetic (NOD) mouse due to a mutation in their shared bidirectional promoter," J Immunol. 159:3068-3080 (1997).
Yang et al., "Effect of tumor necrosis factor alpha on insulin-dependent diabetes mellitus in NOD Mice. I. The early development of autoimmunity and the diabetogenic process," J Exp Med. 180:995-1004 (1994).
Zulewski et al., "Multipotential nestin-positive stem cells isolated from adult pancreatic islets differentiate ex vivo into pancreatic endocrine, exocrine, and hepatic phenotypes," Diabetes. 50:521-533 (2001).
Zöller et al., "Apoptosis resistance in peripheral blood lymphocytes of alopecia areata patients," Retrieved from Science Direct, published in: J Autoimmun. 23(3):241-256 (2004) (30 pages).
Kühtreiber et al., "Long-term reduction in hyperglycemia in advanced type 1 diabetes: the value of induced aerobic glycolysis with BCG vaccinations," NPJ Vaccines. 3:23 (2018) (14 pages).
Greenbaum et al., "Guidelines for Intervention Trials in Subjects with Newly Diagnosed Type 1 Diabetes," Diabetes. 52 (2003) (7 pages).
Terada et al., "Bone marrow cells adopt the phenotype of other cells by spontaneous cell fusion," Nature. 416:542-545 (2002).
Murthi et al., "Novel homeobox genes are differentially expressed in placental microvascular endothelial cells compared with macrovascular cells," Placenta. 29(7):624-630 (2008) (7 pages).
Faustman et al., "T-lymphocyte changes linked to autoantibodies. Association of insulin autoantibodies with CD4+CD45R+ lymphocyte subpopulation in prediabetic subjects," Diabetes. 40:590-597 (1991).
Baeza et al., "Pancreatic regenerating gene overexpression in the nonobese diabetic mouse during active diabetogenesis," Diabetes. 45(1):67-70 (1996) (4 pages).
Gazda et al., "Diabetes results from a late change in the autoimmune response of NOD mice," J Autoimmun. 10:261-270 (1997).
Anderson et al., "Studies on the cytophilic properties of human beta2 microglobulin," J Immunol. 114(3):997-1000 (1975).
Brayer et al., "Alleles from chromosomes 1 and 3 of NOD mice combine to influence Sjögren's syndrome-like autoimmune exocrinopathy," J. Rheumatol. 27(8):1896-1904 (2000).
Petersen et al., "Bone marrow as a potential source of hepatic oval cells," Science. 284(5417):1168-70 (1999).
Alison et al., "Hepatocytes from non-hepatic adult stem cells," Nature. 406(6793):257 (2000).
Faustman et al., "Stem cells in the spleen: Therapeutic potential for Sjogren's syndrome, type I diabetes, and other disorders," available in PMC Jul. 21, 2014, published in final edited form as: Int J Biochem Cell Biol. 42(10):1576-9 (2010) (8 pages).
Ying et al., "Changing potency by spontaneous fusion," Nature. 416:545-548 (2002).
Faustman et al., "Abnormal T-lymphocyte subsets in Type I Diabetes," Diabetes. 38:1462-1468 (1989).
Schaible, "Long term safety of infliximab," Can J Gastroenterol. 14(Suppl C):29C-32C (2000) (5 pages).
Shakoor et al., "Drug-induced systemic lupus erythematosus associated with etanercept therapy," Lancet. 359(9306):579-80 (2002).
Wicker et al., "Transfer of autoimmune diabetes mellitus with splenocytes from nonobese diabetic (NOD) mice," Diabetes. 35:855-860 (1986).

(56) References Cited

OTHER PUBLICATIONS

Miller et al., "Both the Lyt-2+ and L3T4+ T cell subsets are required for the transfer of diabetes in nonobese diabetic mice," J Immunol. 140(3):52-8 (1988).
McInerney et al., "Prevention of insulitis and diabetes onset by treatment with complete Freund's adjuvant in NOD mice," Diabetes. 40:715-725 (1991).
Bernabeu et al., "Beta2-microglobulin from serum associates with MHC class I antigens on the surface of cultured cells," Nature. 308:642-645 (1984) (4 pages).
Watt et al., "Specific alternative HOX11 transcripts are expressed in paediatric neural tumours and T-cell acute lymphoblastic leukaemia," Gene. 323:89-99 (2003).
Faustman et al., "Linkage of faulty major histocompatibility complex class I to autoimmune diabetes," Science. 254:1756-1761 (1991).
Wellik, "The role of Hox11 paralogous genes in prostate development," Grant Detail. (2009) (1 page)(Abstract only).
Juang et al., "Beneficial influence of glycemic control upon the growth and function of transplanted islets," Diabetes 43:1334-1339 (1994).
Pontesilli et al., "Circulating lymphocyte populations and autoantibodies in non-obese diabetic (NOD) mice: a longitudinal study," Clin Exp Immunol. 70(1):84-93 (1987).
Tamura et al., "In vivo differentiation of stem cells in the aorta-gonad-mesonephros region of mouse embryo and adult bone marrow," Exp Hematol. 30(8):957-966 (2002).
Markmann et al., "Indefinite survival of MHC class I-deficient murine pancreatic islet allografts," Transplantation. 54(6):1085-1089 (1992).
Zhang et al., "An animal study on the preventive intervention for decreasing the incidence of type 1 diabetes mellitus," Chinese Journal of Clinical Rehabilitation. 9(47):58-60 (2005) (English Abstract).
Vermeire et al., "Autoimmunity associated with anti-tumor necrosis factor alpha treatment in Crohn's disease: a prospective cohort study," Gastroenterology. 125(1):32-9 (2003).
Van Dam et al., "BCG lowers plasma cholesterol levels and delays atherosclerotic lesion progression in mice," Atherosclerosis. 251:6-14 (2016).
Yang et al., "A variant of TNFR2-Fc fusion protein exhibits improved efficacy in treating experimental rheumatoid arthritis," PLoS Comput Biol. 6(2):e1000669 (2010) (7 pages).
Khalili et al., "Treatment for salivary gland hypofunction at both initial and advanced stages of Sjögren-like disease: a comparative study of bone marrow therapy versus spleen cell therapy with a 1-year monitoring period," Cytotherapy. 16(3):412-23 (2014).
Vagima et al., "MT1-MMP and RECK are involved in human CD34+ progenitor cell retention, egress, and mobilization," J Clin Invest. 119(3):492-503 (2009).
Faustman, "EBV infection and anti-CD3 treatment for Type 1 diabetes: bad cop, good cop?" Expert Rev Clin Immunol. 9(2):95-7 (2013).
Blüml et al., "Antiinflammatory effects of tumor necrosis factor on hematopoietic cells in a murine model of erosive arthritis," Arthritis Rheum. 62(6):1608-19 (2010).
Almoallim et al., "Anti-tumor necrosis factor-alpha induced systemic lupus erythematosus," Open Rheumatol J. 6:315-9 (2012).
Zachs et al., "Noninvasive ultrasound stimulation of the spleen to treat inflammatory arthritis," Nat Commun. 10:951 (2019) (10 pages).
Chen et al., "Contrasting effects of TNF and anti-TNF on the activation of effector T cells and regulatory T cells in autoimmunity," available in PMC Dec. 1, 2012, published in final edited form as: FEBS Lett. 585(23):3611-8 (2011) (16 pages).
Khalili et al., "Mesenchymal stromal cells improve salivary function and reduce lymphocytic infiltrates in mice with Sjögren's-like disease," PLoS One. 7(6):e38615 (2012) (11 pages).
Chi-Chieh Lai et al., "Reaction at the Bacillus Calmette-Guerin Inoculation Site in Patients with Kawasaki Disease," Pediatr Neonatol. 54(1):43-8 (2013).
Alexandroff et al.,: "BCG immunotherapy of bladder cancer: 20 years on," Lancet. 353(9165):1689-94 (1999).
Dong et al., "Essential protective role of tumor necrosis factor receptor 2 in neurodegeneration," Proc Natl Acad Sci USA. 113(43):12304-9 (2016).
Madsen et al., "Oligodendroglial TNFR2 mediates membrane TNF-dependent repair in experimental autoimmune encephalomyelitis by promoting oligodendrocyte differentiation and remyelination," J Neurosci. 36(18):5128-43 (2016).
Brod et al., "New clinical trial in newly diagnosed type 1 diabetes," <www.diabetesstation.org/articles/brod.htm>, Mar. 9, 2001 (2 pages).
Khalili et al., "Bone marrow cells are a source of undifferentiated cells to prevent Sjogren's syndrome and to preserve salivary glands function in the non-obese diabetic mice," available in PMC Jun. 13, 2013, published in final edited form as: Int J Biochem Cell Biol. 42(11):1893-9 (2010) (18 pages).
Canas et al., "A randomized, double blind, placebo-controlled pilot trial of the safety and efficacy of atorvastatin in children with elevated low-density lipoprotein cholesterol (LDL-C) and type 1 diabetes," Pediatr Diabetes. 16(2):79-89 (2015).
Gylling et al., "Cholesterol metabolism in type 1 diabetes," Diabetes. 53(9):2217-22 (2004).
Diaz et al., "Loss of lineage antigens is a common feature of apoptotic lymphocytes," J Leukoc Biol. 76(3):609-15 (2004).
Baxter et al., "Mycobacteria precipitate an SLE-like syndrome in diabetes-prone NOD mice," Immunol. 83(2):227-31 (1994).
Nwosu et al., "Abnormalities in Serum Lipids and Liver Function in Nigeria Patients with Leprosy," JOMIP. 2(2001):5-10 (2004).
Sula, "The part played by BCG vaccination in reducing the morbidity and mortality rates from tuberculosis in Czechoslovakia," Rev Czech Med. 2(2):127-35 (1956).
Navarro, "Nuestra Experiencia en la vacunacion," Boletin Med Univ Autonoma Guadalajara. 3(2):24-31 (1963) (1 page).
Tamura et al., "In vivo differentiation of stem cells in the aorta-gonad-mesonephros region of mouse embryo and adult bone marrow," Exp Hematol. 30(8):957-966 (2002) (Abstract Only) (2 pages).
Waters et al., "Annual Immunotherapy in Treated Lepromatous Leprosy With 3 Different BCG-Based Vaccines—A 6 Year Assessment," Int J Lepr Other Mycobact Dis. 61(4):103A-104A (1993).

\* cited by examiner

SEQUENCE LISTING

```
<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: Synthetic Construct

<400> SEQUENCE: 1

His Leu Val Glu Ala Leu Tyr Leu Val
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic Construct

<400> SEQUENCE: 2

Lys Ile Phe Gly Ser Leu Ala Phe Leu
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Construct

<400> SEQUENCE: 3

Asn Leu Val Pro Met Val Ala Thr Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic Construct
```

```
<400> SEQUENCE: 4

Gly Leu Cys Thr Leu Val Ala Met Leu
1               5
```

METHODS OF IDENTIFYING SUBJECTS RESPONSIVE TO TREATMENT FOR TYPE 1 DIABETES AND COMPOSITIONS FOR TREATING THE SAME

SEQUENCE LISTING

The instant application contains a Sequence Listing submitted via EFS-Web and hereby incorporated by reference in its entirety. Said ASCII copy, created on Jan. 24, 2019, is named 00786-569002_Sequence_Listing_1.24.19_ST25.txt, and is 1,197 bytes in size.

FIELD OF THE INVENTION

In general, the present invention relates to methods of identifying subjects having an autoimmune disease that are likely to respond to treatment with a TNF-α receptor II activator and methods of treating the subjects identified as likely to respond to the treatment. The invention also provides methods for treating subjects that are determined to be unlikely to respond to TNF-α receptor II activator treatment alone.

BACKGROUND

Autoimmune diseases are believed to involve immune responses to the body's own components that are not observed under normal conditions, which result in a pathological state that causes various tissue disorders and/or functional disorders. Autoimmune diseases are broadly classified into systemic autoimmune diseases and organ-specific autoimmune diseases according to their characteristics. Examples of autoimmune diseases include insulin-dependent diabetes (also known as type 1 diabetes), systemic lupus erythematosus, chronic rheumatoid arthritis, Hashimoto's disease, alopecia areata, ankylosing spondylitis, antiphospholipid syndrome, autoimmune Addison's disease, autoimmune hemolytic anemia, autoimmune hepatitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, ulcerative colitis, psoriatic arthritis, essential mixed cryoglobulinemia, fibromyalgia-fibromyositis, Graves' disease, Guillain-Barré, hypothyroidism, idiopathic pulmonary fibrosis, idiopathic thrombocytopenia purpura (ITP), IgA nephropathy, juvenile arthritis, lichen planus, lupus, Ménière's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, sarcoidosis, scleroderma, Sjögren's syndrome, Stiff-Man syndrome, Devic's disease, Takayasu arteritis, temporal arteritis/giant cell arteritis, ulcerative colitis, uveitis, vasculitis, vitiligo, Wegener's granulomatosis, and autoimmune neurological disorders (e.g., autoimmune Alzheimer's disease, autoimmune Parkinson's disease, or amyotrophic lateral sclerosis).

In particular, type 1 diabetes is a severe, childhood, autoimmune disease, characterized by insulin deficiency that prevents normal regulation of blood glucose levels. Insulin is a peptide hormone produced by B cells within the islets of Langerhans of the pancreas (β-islet cells). Insulin promotes glucose utilization, protein synthesis, formation and storage of neutral lipids, and is the primary source of energy for brain and muscle tissue. Type 1 diabetes is caused by an autoimmune reaction that results in complete destruction of the β-islet cells of the pancreas, which eliminates insulin production and eventually results in hyperglycemia and ketoacidosis. Insulin injection therapy has been useful in preventing severe hyperglycemia and ketoacidosis, but fails to completely normalize blood glucose levels. Although insulin injection therapy has been quite successful, it does not prevent the premature vascular deterioration that is the leading cause of morbidity among diabetics today. Diabetes-related vascular deterioration, which includes both microvascular deterioration and acceleration of atherosclerosis, can eventually cause renal failure, retinal deterioration, angina pectoris, myocardial infarction, peripheral neuropathy, and atherosclerosis.

C-peptide, or connecting peptide, is a short 31 amino-acid protein that connects the A-chain and B-chain of insulin within the proinsulin molecule. β-Islet cells of the pancreas secrete preproinsulin containing an A-chain, a C-peptide, a B-chain, and a signal sequence. The signal sequence is cleaved to yield proinsulin. Subsequently, C-peptide is cleaved to produce the mature insulin protein, which contains the disulfide-linked A-chain and B-chain. Newly diagnosed diabetes patients are often stratified into those having type 1 diabetes and type 2 diabetes based on their C-peptide levels. Measurement of C-peptide levels in a subject constitutes a useful proxy test for insulin production in the body of the subject, as variability of insulin levels within the circulatory system of a subject due to liver metabolism renders the measurement of insulin levels inconclusive. C-peptide levels, on the other hand, are minimally affected by liver metabolism. Consequently, peripheral C-peptide concentrations reflect the secretion of insulin by β-islet cells more accurately than insulin concentration.

HbA1c (glycated hemoglobin or glycosylated hemoglobin) is a form of hemoglobin that is produced in vivo by a non-enzymatic glycation of hemoglobin in plasma. The ratio of HbA1c to non-glycated forms of hemoglobin is directly correlated to the glucose concentration in plasma. Therefore, high levels of HbA1c observed over a prolonged period of time in a sample from a diabetic may be indicative of a serious condition, such as hyperglycemia (e.g., acute hyperglycemia).

Tumor necrosis factor-alpha (TNF-α) is a naturally occurring cytokine that was described in 1975 as the serum factor induced after Bacillus Calmette-Guérin (BCG) injection as a means to fight tumors (Carswell et al., *Proc. Natl. Acad. Sci. U.S.A.* 72:3666-3670, 1975). The cloning of TNF-α and its two receptors uncovered sequence homology to the genomes of microbial pathogens (e.g., Loetscher et al., *Cell* 62:351, 1990). This surprising sequence overlap represents a system of intricate microbial responses to modulate host TNF-α secretion and the activity of its receptors (Rahman et al., *PloS Pathogens* 2:66, 2006).

TNF-α expression is induced by diverse bacteria, parasites, and viruses as a host first line defense to infections. Viruses, such as the Epstein-Barr virus, encode receptors and proteins that even augment TNF-α and TNF-α signaling (Liebowitz, *New Engl. J. Med.* 338:1461-1463, 1998; Guasparri et al., *Blood* 111:3813-3821, 2008; Wang et al., *Cell* 43:831-840, 1985). Alternatively, a variety of viruses have been shown to express proteins that repress TNF-α signaling activity and function in the host (Rahman et al., *PloS Pathogens* 2:66, 2006). Some evidence suggests that viral infections (e.g., Epstein-Barr virus infections) may cause autoimmune disease (Sairenji et al., *Diabetologia* 34:33-39, 1991).

Although a number of investigated therapies against autoimmune diseases have demonstrated some palliative or even curative properties, these therapies may not produce consistently beneficial outcomes in all subjects having an autoimmune disease, such as type 1 diabetes. Therefore, there remains a need for methods to accurately identify subjects that are likely to respond to a treatment or a set of treatments prior to treating these subjects, as well as therapies for treating subjects identified as likely to respond to the treatment.

SUMMARY OF THE INVENTION

In the first aspect, the invention provides a method of determining the likelihood a subject having an autoimmune disease will respond to treatment with a tumor necrosis factor-α (TNF-α) receptor II (TNFR2) activator. The method involves:
  (i) contacting an in vitro biological sample comprising a population of $CD8^+$ T cells from the subject with a composition comprising a TNFR2 activator; and
  (ii) measuring CD8 protein density on the surface of autoreactive $CD8^+$ T cells in the population;
where reduced CD8 protein density on the surface of the autoreactive $CD8^+$ T cells relative to a reference $CD8^+$ T cell indicates the subject is likely to respond to the treatment. In some embodiments, the reference $CD8^+$ T cell is from a reference sample from a subject having an autoimmune disease and not being treated or pretreated with a TNFR2 activator. In other embodiments, the reference $CD8^+$ T cell is from a reference sample from a healthy subject. In certain embodiments, the measuring is performed using anti-CD8 antibody, which may be conjugated to a fluorochrome. In particular embodiments, the biological sample is incubated with dasatinib prior to the contacting (e.g., the biological sample is incubated with dasatinib for at least 4 hours, and/or the biological sample is incubated with dasatinib for at most 48 hours).

In some embodiments of the methods of the invention, the autoimmune disease is type 1 diabetes, alopecia areata, ankylosing spondylitis, antiphospholipid syndrome, autoimmune Addison's disease, autoimmune hemolytic anemia, autoimmune hepatitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, systemic lupus erythematosous, ulcerative colitis, psoriatic arthritis, essential mixed cryoglobulinemia, fibromyalgia-fibromyositis, Graves' disease, Guillain-Barré, Hashimoto's thyroiditis, hypothyroidism, idiopathic pulmonary fibrosis, idiopathic thrombocytopenia purpura (ITP), IgA nephropathy, juvenile arthritis, lichen planus, lupus, Ménière's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, Stiff-Man syndrome, Devic's disease, Takayasu arteritis, temporal arteritis/giant cell arteritis, ulcerative colitis, uveitis, vasculitis, vitiligo, Wegener's granulomatosis, or an autoimmune neurological disorder. In certain embodiments, the autoimmune disease is type 1 diabetes, celiac sprue-dermatitis, Crohn's disease, Graves' disease, hypothyroidism, lupus, multiple sclerosis, psoriasis, rheumatoid arthritis, sarcoidosis, Sjögren's syndrome, or ulcerative colitis. In particular embodiments, the autoimmune neurological disorder is autoimmune-mediated damage to neurons, autoimmune Alzheimer's disease, autoimmune Parkinson's disease, or autoimmune-mediated amyotrophic lateral sclerosis.

In the second aspect, the invention provides a method of determining the likelihood a subject having type 1 diabetes will respond to treatment with a tumor necrosis factor-α (TNF-α) receptor II (TNFR2) activator. The method involves contacting an in vitro biological sample from the subject with a device capable of detecting C-peptide in the sample, where a detectable C-peptide level in the sample indicates the subject is likely to respond to the treatment, and where a substantially undetectable C-peptide level indicates the subject is unlikely to respond to the treatment. In some embodiments, a substantially undetectable level of the C-peptide indicates the subject should be excluded from the treatment. In certain embodiments, the substantially undetectable level is a C-peptide level less than about 1.5 pmol/L (e.g., less than about 1.0 pmol/L). In other embodiments, the detectable level is a C-peptide level of greater than about 1.5 pmol/L. In specific embodiments, the subject is identified as likely to respond to the treatment if the concentration of C-peptide is in the range of about 1.5 pmol/L to about 4.0 pmol/L.

In certain embodiments of this aspect of the invention, the contacting is performed prior to the treatment of the subject. The contacting involves:
  (i) contacting the sample with the device having an immobilized capture agent on the surface thereof so that the C-peptide in the sample binds to the immobilized capture agent;
  (ii) contacting the surface with a detecting binding agent so that the C-peptide binds to the detecting binding agent; and
  (iii) measuring the level of the C-peptide in the sample using the detecting binding agent.

In some embodiments, the detecting binding agent includes peroxidase enzyme. In particular embodiments, the measuring involves contacting the surface with a solution containing hydrogen peroxide and a peroxidase substrate.

In some embodiments of this aspect of the invention, the method of the invention further involves measuring a reference HbA1c level in a blood sample from the subject prior to initiating the treatment. The method involves:
  (i) measuring HbA1c level in a blood sample taken from the subject after the treatment,
  (ii) comparing the HbA1c level to the reference HbA1c level, and
  (iii) identifying the subject as in need of a repeat treatment with the one or more TNFR2 activators if the HbA1c level is equal to or greater than the reference HbA1c level.

In particular embodiments of the invention, the blood sample is taken from the subject at least 6 months after the treatment (e.g., at least 1 year after the treatment, at least 2 years after the treatment, at least 3 years after the treatment, or at least 5 years after the treatment).

In particular embodiments of any of the aspects of the invention, the sample contains blood, a blood component, or urine. In certain embodiments, the blood component is serum or plasma. In other embodiments, the sample contains urine.

In some embodiments of any of the aspects of the invention, the TNFR2 activator is Bacillus Calmette-Guérin (BCG), complete Freund's adjuvant, TNF-α, a TNF-α receptor II agonist, a TNF-α mutein, interleukin-1, interleukin-2, tissue plasminogen factor, lipopolysaccharide (LPS), lymphotoxin, or cachectin. In particular embodiments, TNFR2 activator is BCG. In certain embodiments, the autoimmune disease is type 1 diabetes, and the method is used in combination with one or more methods of the second aspect of the invention.

In the third aspect, the invention provides a pharmaceutical composition containing one or more TNFR2 activators for use in treating an autoimmune disease in a subject diagnosed as likely to respond to the treatment. In particular embodiments, a sample from the subject contains a population of T cells having reduced CD8 protein density on the surface thereof following exposure to a TNFR2 activator, relative to CD8 protein density on the surface of a reference T cell in a sample from a reference subject (e.g., a healthy subject or a subject having an autoimmune disease and not being treated or pretreated with one or more TNFR2 activators). In some embodiments, the subject is identified as likely to respond to the treatment according to the method of the first aspect of the invention.

In some embodiments of this aspect of the invention, the autoimmune disease is type 1 diabetes, alopecia areata, ankylosing spondylitis, antiphospholipid syndrome, autoimmune Addison's disease, autoimmune hemolytic anemia, autoimmune hepatitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, systemic lupus erythmatosous, ulcerative colitis, psoriatic arthritis, essential mixed cryoglobulinemia, fibromyalgia-fibromyositis, Graves' disease, Guillain-Barré, Hashimoto's thyroiditis, hypothyroidism, idiopathic pulmonary fibrosis, idiopathic thrombocytopenia purpura (ITP), IgA nephropathy, juvenile arthritis, lichen planus, lupus, Ménière's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, Stiff-Man syndrome, Devic's disease, Takayasu arteritis, temporal arteritis/giant cell arteritis, ulcerative colitis, uveitis, vasculitis, vitiligo, Wegener's granulomatosis, or an autoimmune neurological disorder. In some embodiments, the autoimmune disease is type 1 diabetes, celiac sprue-dermatitis, Crohn's disease, Graves' disease, hypothyroidism, lupus, multiple sclerosis, psoriasis, rheumatoid arthritis, sarcoidosis, Sjögren's syndrome, or ulcerative colitis. In particular embodiments, the autoimmune neurological disorder is autoimmune-mediated damage to neurons, autoimmune Alzheimer's disease, autoimmune Parkinson's disease, or autoimmune-mediated amyotrophic lateral sclerosis.

In the fourth aspect, the invention provides a pharmaceutical composition containing one or more TNFR2 activators for use in treating type 1 diabetes in a subject identified as likely to respond to the treatment prior to the treating by determining a level of C-peptide in an in vitro sample from the subject, where a substantially undetectable C-peptide level indicates the subject is unlikely to respond to the treatment, and where a detectable C-peptide level indicates the subject is likely to respond to the treatment. In particular embodiments, the substantially undetectable C-peptide level indicates the subject should be excluded from the treatment. In some embodiments, the substantially undetectable level is a C-peptide level less than 1.5 pmol/L. In other embodiments, the detectable level is a C-peptide less of greater than 1.5 pmol/L. In certain embodiments, the subject is excluded from the treating if a urine sample from the subject exhibits a C-peptide to creatinine ratio of less than about 4.0 pmol/mmol. In yet other embodiments, the subject is identified as likely to respond to the treatment if a urine sample from the subject exhibits a C-peptide to creatinine ratio of greater than or equal to about 4.0 pmol/mmol. In particular embodiments, the subject is identified as likely to respond to the treatment according to the methods of the second aspect.

In some embodiments of this aspect, the pharmaceutical composition is characterized in that HbA1c levels of the subject decrease by at least 0.1% within about 4 years after administration of the composition. In other embodiments, the pharmaceutical composition is characterized in that HbA1c levels of the subject decrease by at least 0.1% within about 3 years after administration of the composition. In specific embodiments, the composition is for use in treating type 1 diabetes in the subject a second or subsequent time, where HbA1c levels in the subject increase or remain the same relative to HbA1c level in the subject prior to the previous treatment. In particular embodiments, the subject is identified as in need of a repeat treatment with one or more TNFR2 activators according to the method of the second aspect. In some embodiments, the subject is a human. In other embodiments, the subject is a long term diabetic.

In some embodiments of any of the aspects of the invention, the one or more TNFR2 activators are selected from Bacillus Calmette-Guerin (BCG), complete Freund's adjuvant, TNF-α, a TNF-α receptor II agonist, a TNF-α mutein, interleukin-1, interleukin-2, tissue plasminogen factor, lipopolysaccharide (LPS), lymphotoxin, and cachectin. In particular embodiments, the one or more TNFR2 activators is BCG. In particular embodiments, the composition contains greater than $2\times10^6$ CFU/dose of BCG (e.g., $2.3\times10^6$ CFU/dose of BCG). In specific embodiments, the composition contains less than $4\times10^6$ CFU/dose of BCG. In some embodiments, the composition contains lyophilized BCG. In particular embodiments, the composition contains saline solution of BCG.

In particular embodiments of any of the aspects of the invention, the composition is administered to the subject one or more times (e.g., two or more times, such as twice). In some embodiments, at least two of the administrations of the composition are spaced at least two weeks apart. In other embodiments, at least two of the administrations of the composition are spaced at least four weeks apart.

In certain embodiments of any of the aspects of the invention, the composition is formulated for administration by a route selected from intradermally, intramuscularly, parenterally, intravenously, intra-arterially, intracranially, subcutaneously, intraorbitally, intraventricularly, intraspinally, intraperitoneally, and intranasally. In specific embodiments, the composition is formulated for intradermal administration. In particular embodiments, the composition is formulated for administration as a saline solution. In some embodiments, the solution has a volume of less than about 0.2 cc per dose, such as a volume of 0.1 cc per dose. In some embodiments, the pharmaceutical composition is formulated for separate administration of two or more TNFR2 activators. In other embodiments, the pharmaceutical composition is formulated for combined administration of two or more TNFR2 activators.

In some embodiments of the pharmaceutical composition of the invention, the pharmaceutical composition is characterized as being capable of inducing expression of TNF-α in the subject. In particular embodiments, the pharmaceutical composition is characterized in that the composition is capable of inducing activation of the NF-κB pathway in an autoreactive immune cell (e.g., autoreactive CD8$^+$ T cell) of the subject. In specific embodiments, the pharmaceutical composition is characterized in that the composition causes death of an autoreactive immune cell (e.g., autoreactive CD8$^+$ T cell) in the subject. In certain embodiments, the pharmaceutical composition is characterized in that the composition causes expansion of regulatory T cells (e.g., regulatory CD4$^+$ T cells) in the subject.

In certain embodiments of any of the aspects of the invention, the pharmaceutical composition is characterized in that the composition prevents a complication from hyperglycemia in the subject. In some embodiments, the complication from hyperglycemia is selected from kidney damage, neurological damage, cardiovascular damage, damage to the retina, damage to the feet, damage to the legs, damage to the heart, and ketoacidosis. In specific embodiments, the composition contains one or more pharmaceutically acceptable carriers or excipients.

Definitions

By "about," as used herein, is meant a value that is +10% of the recited value.

By "antibody," as used herein, is meant a whole antibody or immunoglobulin and any antigen-binding fragment or single chain thereof. Antibodies, as used herein, can be mammalian (e.g., human or mouse), humanized, chimeric, recombinant, synthetically produced, or naturally isolated. In most mammals, including humans, whole antibodies have at least two heavy (H) chains and two light (L) chains connected by disulfide bonds. Each heavy chain consists of a heavy chain variable region (abbreviated herein as $V_H$) and a heavy chain constant region. The heavy chain constant region consists of three domains, $C_H1$, $C_H2$, and $C_H3$ and a hinge region between $C_H1$ and $C_H2$. Each light chain consists of a light chain variable region (abbreviated herein as $V_L$) and a light chain constant region. The light chain constant region consists of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. Antibodies of the present invention include all known forms of antibodies and other protein scaffolds with antibody-like properties. For example, the antibody can be a monoclonal antibody, a polyclonal antibody, human antibody, a humanized antibody, a bispecific antibody, a monovalent antibody, a chimeric antibody, or a protein scaffold with antibody-like properties, such as fibronectin or ankyrin repeats. The antibody can have any of the following isotypes: IgG (e.g., IgG1, IgG2, IgG3, and IgG4), IgM, IgA (e.g., IgA1, IgA2, and IgAsec), IgD, or IgE.

By "diabetic," as used herein, is meant a subject diagnosed with type 1 diabetes. In particular, a long-term diabetic is a subject having type 1 diabetes for at least about 5 years (e.g., at least about 6 years, at least about 7 years, at least about 8 years, at least about 9 year, at least 10 years, at least 11 years, at least about 12 years, at least about 13 years, or at least about 14 years) since the onset of type 1 diabetes.

By "Hox11$^+$ splenocyte," as used herein, is meant a pluripotent CD45$^-$ cell expressing the Hox11 gene and found in spleen.

By "immune cell," as used herein, is meant any cell that is involved in the generation, regulation, or effect of the acquired or innate immune system. Immune cells include, e.g., T cells (e.g., CD4$^+$ cells or CD8$^+$ cells), B cells, natural killer (NK) cells, macrophages, monocytes and dendritic cells, and neutrophils.

By "mutein," as used herein, is meant a polypeptide that differs in its amino acid sequence by at least one or more amino acids. For example, a mutein may have an amino acid sequence with greater than 90% but less than 100% sequence identity relative to the amino acid sequence of a reference polypeptide.

By "pharmaceutically acceptable carrier" or "pharmaceutically acceptable excipient," as used interchangeably herein, is meant any ingredient other than the compounds described herein (for example, a vehicle capable of suspending or dissolving the active compound) and having the properties of being nontoxic and non-inflammatory in a patient. Carriers and excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary carriers and excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, xylitol, water, phosphate-buffered saline (PBS), acetate-buffered saline (ABS), Ringer's solution, dextrose, glycerol, ethanol, or the like and combinations thereof.

By "sample," as used herein, is meant any specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject. Preferably, the sample is blood, a blood component (e.g., serum or plasma), or urine.

By "subject" or "patient," as used interchangeably herein, is meant any animal, such as a mammal (e.g., a human). A subject to be treated with a pharmaceutical composition described herein may be one who has been diagnosed by a medical practitioner as having such a condition (e.g., an autoimmune disease, such as type 1 diabetes) or one at risk for developing the condition. Diagnosis may be performed by any technique or method known in the art. One skilled in the art will understand that a subject may have been diagnosed as having an autoimmune disease, such as type 1 diabetes, using a standard test or examination or may have been identified, without examination, as one at high risk due to the presence of one or more risk factors. For type 1 diabetes, such risk factors include, e.g., presence of autoreactive T cells, such as autoreactive $CD8^+$ T cells, fasting plasma glucose levels of at least 6.1 mmol/L, plasma glucose levels of at least 11.1 mmol/L two hours after oral glucose load of 75 g, or decreased serum levels of C-peptide. Before treatment with a pharmaceutical composition of the invention, a subject having an autoimmune disease, such as type 1 diabetes, may be subjected to a diagnostic test described herein in order to determine whether the subject is likely to respond to treatment with the pharmaceutical composition of the invention or as unlikely to respond to the treatment.

By "substantially undetectable C-peptide level," as used herein, is meant that a sample from a subject may have C-peptide levels of less than about 1.5 pmol/L, such as less than about 1.0 pmol/L, or even less than about 0.5 pmol/L. The C-peptide level corresponding to a substantially undetectable C-peptide level does not depend on the feeding state of the subject at the time the sample is obtained. For example, the sample may be from a fasting subject or from a subject that received a stimulus, such as mixed meal tolerance test or stimulation by glucagon test.

By "tumor necrosis factor-α (TNF-α) inducing substance" or "TNF-α inducing substance," as used interchangeably herein, is meant a composition or a molecule that induces expression of tumor necrosis factor-α (TNF-α) in vivo or in vitro. A TNF-α inducing substance may be Bacillus Calmette-Guérin (BCG), complete Freund's adjuvant, interleukin-1, interleukin-2, tissue plasminogen factor, lipopolysaccharide (LPS), lymphotoxin, or cachectin. Preferably, a TNF-α inducing substance is BCG.

By "TNF-α receptor II (TNFR2) agonist" or "TNFR2 agonist," as used interchangeably herein, is meant a composition or a molecule that activates TNFR2 upon binding in vivo or in vitro. Examples of TNFR2 agonists include TNFR2 agonist antibodies and TNF muteins that specifically bind and activate TNFR2.

By "TNF-α receptor II (TNFR2) activator" or "TNFR2 activator," as used interchangeably herein, is meant a composition that directly or indirectly activates TNFR2 in vivo or in vitro. A TNFR2 activator may activate TNFR2 directly, such as by binding TNFR2, or indirectly, such as by inducing the expression of TNF-α. TNFR2 activators include TNF-α, TNF-α inducing substances, and TNFR2 agonists.

DETAILED DESCRIPTION

Figure 1A:
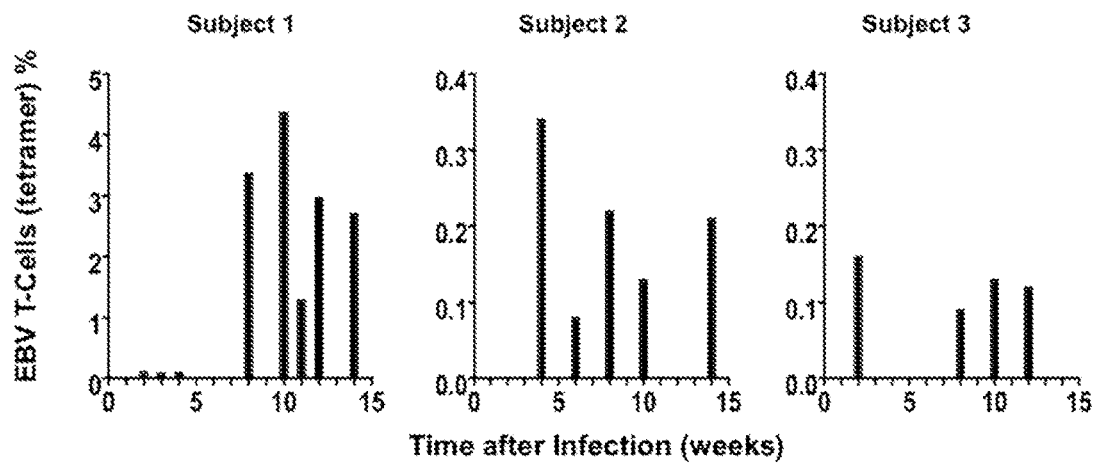
FIG. 1A is a set of three graphs presenting time course data showing the appearance of EBV-specific T-cells in Subject 1, Subject 2, and Subject 3. In each of the graphs, time point 0 indicates the estimated occurrence of EBV infection based on the timing of the appearance of antibodies directed against EBV.

I have discovered methods for determining whether subjects having an autoimmune disease will be likely to respond to treatment with a TNF-α receptor II (TNFR2) activator or unlikely to respond to treatment with a TNF-α receptor II (TNFR2) activator. According to the methods of the invention, the presence, in a sample from a subject having an autoimmune disease, of a population of autoreactive $CD8^+$ T cells exposed in vivo or in vitro to one or more TNF-α receptor II (TNFR2) activators that exhibit a reduced CD8 protein density on their surface may indicate that the subject is likely to respond to treatment with one or more TNFR2 activators. The reduction in CD8 protein density on the surface of autoreactive $CD8^+$ T cells exposed to one or more TNFR2 activators may be relative to the CD8 protein density on the surface of a reference $CD8^+$ T cell. The reference $CD8^+$ T cell may be from a sample from a subject having an autoimmune disease and not being treated or pretreated in vivo or in vitro with a TNFR2 activator. Alternatively, the reference $CD8^+$ T cell may be from a sample from a healthy subject. According to the methods of the invention, the CD8 protein density on the surface of a $CD8^+$ T cell may be determined using an anti-CD8 antibody.

I have also discovered methods of discriminating between subjects having type 1 diabetes that are likely to respond to treatment with a TNF-α receptor II (TNFR2) activator and subjects having type 1 diabetes that are not likely to respond to treatment with a TNFR2 activator. I have discovered that C-peptide levels in a subject can be used to assess the likelihood the subject will respond to treatment, in particular, to treatment with a TNFR2 activator. A subject having type 1 diabetes with a detectable level of C-peptide (e.g., a level of greater than or equal to about 1.5 pmol/L) is likely to respond to treatment with a pharmaceutical composition containing a TNFR2 activator. In particular, a response to treatment with a TNFR2 activator may be assessed by detecting an increase in C-peptide levels in the subject following treatment with a TNFR2 activator. On the other hand, a subject having type 1 diabetes with a substantially undetectable level of C-peptide (e.g., a level of less than about 1.5 pmol/L) is unlikely to respond to treatment with a pharmaceutical composition containing a TNFR2 activator (e.g., the subject may be excluded from such therapy or may be administered TNFR2 therapy in combination with a cellular therapy, such as therapy with a pluripotent cell (e.g., a Hox11+ cell)).

C-peptide levels may be assayed using a sample from the subject, such as blood, a blood component (serum or plasma), or urine. Measurement of C-peptide levels is possible using any method known in the art, such as enzyme-linked immunosorbent assay (ELISA), which is described in Thermo Scientific Pierce Assay Development Technical Handbook, Version 2, 2011, the disclosure of which is incorporated herein by reference.

The use of a TNFR2 activator in treating, e.g., type 1 diabetics having detectable C-peptide levels is predicated on the discovery that β-islet cells in the pancreas may be restored or regenerated over time if damage to these cells can be reduced (e.g., by reducing the number of autoreactive T cells that target β-islet cells). Subjects having type 1 diabetes with substantially undetectable C-peptide levels may not be capable of restoring or regenerating β-islet cells in the pancreas unlike subjects with detectable C-peptide levels. This is likely due to the loss of many or even substantially all of the β-islet cells as a result of the disease (e.g., a subject with substantially undetectable C-peptide levels likely has an insufficient number of the β-islet cells remaining in their body, and thus would be unable to establish normoglycemia even in the absence of cell injury due to autoreactive immune cells). Moreover, the restoration or regeneration of β-islet cells may be related to the differentiation potential of pluripotent cells (e.g., Hox11+ splenocytes) residing in the subject, which may provide a source of cells that can produce a variety of cell types, including β-islet cells. A substantially undetectable C-peptide level in a subject may also indicate that the subject lacks a sufficient number of these pluripotent cells, such as Hox11+ splenocytes, to restore or regenerate β-islet cells and to establish normoglycemia.

The beneficial activity of TNFR2 activators in subjects having type 1 diabetes with detectable C-peptide levels relates to their ability to kill autoreactive CD8+ T cells in vivo (see, e.g., Ban et al., *Proc. Nat. Acad. Sci, USA,* 105:13644-13649, 2008, which is incorporated herein by reference), which reduces or minimizes tissue damage caused by these cells (e.g., the loss of β-islet cells). TNFR2 activators also promote expansion of beneficial regulatory CD4+ T cells in vivo, which modulates the inflammatory component of the disease. Without being bound by any particular theory, it is believed that TNFR2 agonism activates intracellular NF-κB signaling, which is believed to induce apoptosis in autoreactive T cells, thereby treating type 1 diabetes in subjects (e.g., humans) administered the TNFR2 activator.

Diagnostic Methods of the Invention
CD8 Surface Protein Assay

The present invention features methods of identifying a subject (e.g., a human) having an autoimmune disease as being likely to respond to treatment with one or more TNFR2 activators. In some embodiments, the method involves: (i) contacting an in vitro biological sample (e.g., blood) containing one or more CD8+ T cells from the subject with a composition containing a TNFR2 activator, and (ii) detecting autoreactive CD8+ T cells using an anti-CD8 antibody. A reduced CD8 protein density on the surface of one or more of the autoreactive CD8+ T cells relative to a reference CD8+ T cell indicates the subject is likely to respond to the treatment. The reference CD8+ T cell, such as an autoreactive CD8+ T cell, may be from a sample from a subject having an autoimmune disease and not being treated or pretreated in vivo or in vitro with a TNFR2 activator. Alternatively, the reference CD8+ T cell (e.g., non-autoreactive CD8+ T cell) may be from a sample from a healthy subject.

The sample (e.g., blood) containing one or more autoreactive CD8+ T cells for analysis of CD8 protein density on their surface may be obtained from a subject having an autoimmune disease. The sample can be preserved with a tyrosine kinase inhibitor, such as dasatinib (Axon Medchem BV, Groningen, the Netherlands) (see Lissina et al., *J. Immunol. Methods,* 340:11-24, 2009, which is incorporated herein by reference), which metabolically "freezes" the cells in the sample. The end concentration of dasatinib in the sample may be at least about 10 nM (e.g., at least about 50 nM, at least about 100 nM, at least about 200 nM, at least about 500 nM, or at least about 1 µM). To preserve CD8+ T cells, the sample containing these cells and the tyrosine kinase inhibitor may be incubated for at least about 4 h (e.g., at least about 6 h, at least about 8 h, at least about 10 h, at least about 12 h, or at least about 14 h) and up to about 48 h (e.g., up to about 40 h, up to about 36 h, up to about 32 h, up to about 28 h, up to about 24 h, or up to about 20 h) prior to conducting a determination of cell-surface CD8 protein density using the cells in the sample. Dasatinib is a metabolic inhibitor that does not alter the cell surface structures. Therefore, cells preserved with dasatinib can be accurately stained even if stored for 4-48 hours.

The sample (whether fresh or preserved with a tyrosine kinase inhibitor, such as dasatinib) may be analyzed, e.g., by contacting the sample with an anti-CD8 antibody conjugated to any fluorochrome known in the art. Non-limiting examples of fluorochromes include FITC, RD1, allophycocyanin (APC), a CF™ dye (Biotium, Hayward, CA), BODIPY (INVITROGEN™ of Life Technologies, Carlsbad, CA), ALEXA FLUOR® (INVITROGEN™ of Life Technologies, Carlsbad, CA), DyLight Fluor (Thermo Scientific Pierce Protein Biology Products, Rockford, IL), ATTO (ATTO-TEC GmbH, Siegen, Germany), FluoProbe (Interchim SA, Motlucon, France), and Abberior Probes (Abberior GmbH, Göttingen, Germany). Methods, such as flow cytometry, may be used to detect fluorescence from a fluorochrome conjugated to an anti-CD8 antibody that is attached to the CD8 protein on the surface of an autoreactive T cell. The intensity of the fluorescence provides a quantitative measure of the CD8 protein density on the surface of the cell.

The detection of a decrease in cell-surface CD8 protein density of a population of autoreactive CD8+ T cells, following exposure to a TNFR2 activator, indicates the subject is likely to respond to treatment for an autoimmune disease using the TNFR2 activator. A reduction in cell-surface CD8 protein density on autoreactive CD8+ T cells, relative to a reference CD8+ T cell, indicates the autoreactive CD8+ T cells are undergoing apoptosis resulting from treatment with the TNFR2 activator. The reference CD8+ T cell may be a non-autoreactive CD8+ T cell from a healthy subject. Alternatively, the reference CD8+ T cell may be an autoreactive CD8+ T cell that has not been exposed to a TNFR2 activator in vivo or in vitro. Thus, a decrease in CD8 cell-surface density detected using the assay described above indicates a subject is likely to respond to in vivo therapy with a TNFR2 activator, which would be expected to cause autoreactive CD8$^+$ T cell death during treatment. The absence of viable autoreactive CD8$^+$ T cells would promote a decrease in cellular damage caused by these cells and possibly regeneration of damaged tissues, which may improve the health of the subject.

C-Peptide Assay

The present invention also features methods of identifying a subject (e.g., a human) having type 1 diabetes as being likely to respond to treatment with one or more TNFR2 activators. The method involves contacting an in vitro biological sample (e.g., blood, a blood component (such as serum or plasma), or urine) from the subject (e.g., a human) with a device capable of detecting C-peptide in the sample. The detection of a level of C-peptide in the sample of greater than about 1.5 pmol/L (e.g., greater than about 2.5 pmol/L) indicates that the subject (e.g., a human) is likely to respond to the treatment. The detection of a level of C-peptide in the sample of less than about 1.5 pmol/L indicates that the subject is unlikely to respond to the treatment (e.g., the subject may be excluded from such therapy or may be administered TNFR2 therapy in combination with a cellular therapy (e.g., a pluripotent cell, such as a Hox11$^+$ splenocyte)). The detection of a level of C-peptide in the sample in the range of about 1.5 pmol/L to about 900 pmol/L (e.g., about 500 pmol/L, about 200 pmol/L, about 100 pmol/L, about 50 pmol/L, or about 4.0 pmol/L) indicates that the subject is likely to respond to the treatment. According to the methods of the invention, the subject may be a long term diabetic. A C-peptide level of greater than 1.5 pmol/L indicates the subject is likely to respond to treatment with a TNFR2 activator. A C-peptide level may be measured in either a sample from a fasting subject (fasting C-peptide level) or a sample from a subject in a mixed meal tolerance test or stimulation by glucagon test. A subject would be responsive to treatment with a TNFR2 activator if the treatment causes cell death of autoreactive CD8$^+$ T cells and/or expansion or regeneration of endogenous β-islet cells, thereby leading to an increase in insulin levels and a decrease of average plasma glucose levels (e.g., to establish normoglycemia), relative to the levels prior to the treatment.

According to the methods of the invention, the contacting step may be performed by: (i) contacting the sample with the device having an immobilized capture agent (e.g., an antibody that binds C-peptide) on its surface so that C-peptide in the sample binds to the immobilized capture agent; (ii) contacting the surface with a detecting binding agent so that C-peptide binds to the detecting binding agent (e.g., an antibody that binds C-peptide specifically); and (iii) detecting the level of C-peptide in the sample using the detecting binding agent. The detecting binding agent may be specific to C-peptide. The detecting binding agent may be conjugated to a peroxidase enzyme, which can be detected by contacting the surface of the device with a solution of hydrogen peroxide. The solution of hydrogen peroxide may further contain a peroxidase substrate. According to the methods of the invention, any peroxidase substrate known in the art may be used. Some common peroxidase substrates are 2,2'-azino-bis(3-ethylbenzothiazoline-6-sulphonic acid) (ABTS), 3,3',5,5'-tetramethyl-benzidine (TMB), o-phenylenediamine dihydrochloride (OPD), 10-acetyl-3,7-dihydroxyphenoxazine (ADHP), luminol, disodium p-nitrophenyl phosphate (PNPP), o-nitrophenyl-β-galactopyranosidase (ONPG), QuantaBlu fluorogenic peroxidase substrate (Thermo Scientific Pierce Protein Biolody Products, Rockford, IL), QuantaRed enhanced chemifluorescent peroxidase substrate (Thermo Scientific Pierce Protein Biolody Products, Rockford, IL), SUPERSIGNAL™ ELISA femto maximum sensitivity substrate (Thermo Scientific Pierce Protein Biology Products, Rockford, IL), and SUPERSIGNAL™ ELISA pico chemiluminescent substrate (Thermo Scientific Pierce Protein Biology Products, Rockford, IL). The reaction of peroxidase substrates with peroxidase may be detected spectrophotometrically.

Detection of C-peptide in a sample from a subject may be performed using any assay known in the art. For example, ultrasensitive C-peptide Enzyme-Linked Immunosorbent Assay (ELISA), such as the one manufactured by Mercodia AB (Uppsala, Sweden), provides a solid phase two-site enzyme immunoassay for the quantitative determination of C-peptide in a sample. The immunoassay is based on the direct sandwich technique, in which two monoclonal antibodies are directed against separate antigenic determinants on the C-peptide molecule. During incubation, C-peptide in the sample reacts with anti-C-peptide antibodies bound to the microtitration well. After washing, peroxidase (e.g., horseradish peroxidase) conjugated anti-C-peptide antibodies are added. After a second incubation and a simple washing step, the bound conjugate may be detected by a reaction of hydrogen peroxide with 3,3',5,5'-tetramethylbenzidine (TMB). The reaction is stopped by adding acid to give an endpoint that is read spectrophotometrically. Alternatively, after a second incubation the bound conjugate may be detected by any other peroxidase substrate known in the art, such as the substrates listed above.

According to the methods of the invention, a substantially undetectable level of C-peptide in a sample from a subject having type 1 diabetes may indicate that the subject has lost the ability to regenerate β-islet cells, in particular, if the C-peptide level is lower than about 1.5 pmol/L. A substantially undetectable C-peptide level may also indicate that the subject lacks Hox11$^+$ splenocytes capable of regenerating β-islet cells.

Long term efficacy of type 1 diabetes treatment with a TNFR2 activator may be gauged by the ability of the subject to regenerate β-islet cells and/or to reduce the incidence of hyperglycemia and hypoglycemia relative to the incidence of hyperglycemia and hypoglycemia in the subject before the treatment (e.g., efficacy may be gauged by an increase in the duration of time the subject is in a normoglycemic state). The treatment involves administering to the subject a pharmaceutical composition of the invention, such as a composition containing one or more TNFR2 activators, a composition containing one or more pluripotent cells (e.g., Hox11$^+$ splenocytes), or a combination thereof. C-peptide levels may be used as a proxy to assess the efficacy of treatment with a pharmaceutical composition of the invention in a treated subject. A change (e.g., an increase) in C-peptide levels in a subject treated with a pharmaceutical composition of the invention indicates the subject has responded to the treatment. An increase in the C-peptide levels in the subject of about 1% (e.g., about 2%, about 5%, about 10%, about 20%, about 30%, about 40%, about 50%, about 100%, about 200%, about 500%, about 1000%, about 2000%, about 5000%, or about 7000%), at least 1 month (e.g., at least 3 month, at least 6 months, at least 1 year, at least 2 years, at least 3 years, at least 4 years, at least 5 years, or at least 6 years) after treatment of the subject, may indicate the successful treatment of the subject and that no repeat treatment is necessary. A decrease or a lack of a change in the C-peptide levels in a subject, at least 1 month (e.g., at least 3 month, at least 6 months, at least 1 year, at least 2 years, at least 3 years, at least 4 years, at least 5 years, or at least 6 years) after treatment of the subject, may indicate that the subject is in need of a repeat administration of a pharmaceutical composition of the invention. C-peptide levels can be detected at least one month (e.g., at least 3 month, at least 6 months, at least 1 year, at least 2 years, at least 3 years, at least 4 years, at least 5 years, or at least 6 years) after treatment of the subject. Changes in the C-peptide levels may be assessed relative to a reference C-peptide level. The reference C-peptide level may be a C-peptide level detected in a sample taken from the subject prior to a first (or subsequent) treatment with a pharmaceutical composition of the invention.

HbA1c Assay

The invention also features a method of determining whether a subject is or will likely be responsive to a treatment with a TNFR2 activator (alone or in combination with a composition that includes one or more pluripotent cells, such as Hox11$^+$ splenocytes) by measuring the HbA1c level in a blood sample from a subject prior to, during, or after treatment of the subject. HbA1c levels measured prior to treatment of the subject can be used as a reference HbA1c level. Additional measurements of HbA1c levels in a blood sample taken from the subject may be performed at least 1 month (e.g., at least 3 month, at least 6 months, at least 1 year, at least 2 years, at least 3 years, at least 4 years, at least 5 years, or at least 6 years) after treatment of the subject. The methods of the invention may further include comparing the HbA1c level measured after the treatment to the reference HbA1c level, and identifying the subject as in need of a repeat treatment with a pharmaceutical composition of the invention if the HbA1c level is equal to or greater than the reference HbA1c level. After administration of one or more TNFR2 activators, HbA1c levels may be measured in a sample from the subject to determine an endpoint and to assess the long-term success of the treatment. A decrease of at least about 0.1% (e.g., 0.15%, 0.2%, 0.25%, 0.3%, 0.4%, or 0.5%) in HbA1c levels relative to the reference HbA1c level would be indicative of the likely long-term success of the treatment. An increase of at least about 0.1% (e.g., 0.2%, 0.3%, 0.4%, or 0.5%) in HbA1c levels over the reference HbA1c level may indicate that one or more repeat treatments with a pharmaceutical composition of the invention should be given to the subject.

HbA1c level in a blood sample can be measured according to methods known in the art, such as high-performance liquid chromatography, immunoassay, enzymatic assay (Direct Enzymatic HbA1c Assay, Diazyme Laboratories, Poway, CA), capillary electrophoresis (Sebia, Norcross, GA), or boronate affinity chromatography (Trinity Biotech Plc, Bray, Ireland). Methods of measuring HbA1c in a sample from a subject are described in, e.g., Little et al., *Clin. Chem.* 54:1277-1282, 2008, which is incorporated herein by reference. Standard metrics used to describe HbA1c levels are described in, e.g., Goodall, I., *Clin. Biochem. Rev.* 26:5-20, 2005, which is incorporated herein by reference.

Pharmaceutical Compositions of the Invention

The present invention also features pharmaceutical compositions containing one or more TNFR2 activators for use in treating a subject (e.g., a human) having an autoimmune disease (e.g., type 1 diabetes) and, in particular, in treating a subject identified by one or more of the diagnostic methods of the invention as likely to respond to the treatment (e.g., likely to experience CD8$^+$ T cell death and/or likely to experience restoration and/or regeneration of tissues damaged by the autoimmune disease (e.g., β-islet cells in subjects with type 1 diabetes)).

A pharmaceutical composition containing one or more TNFR2 activators may be used in treating an autoimmune disease, such as type 1 diabetes, in a subject that is likely to respond to the treatment. A reduction in the density of CD8 protein on the surface of an autoreactive CD8$^+$ T cell in a sample from the subject having an autoimmune disease, relative to the density of CD8 protein on the surface of a reference T cell, indicates that the subject is likely to respond to treatment with a TNFR2 activator. The reference T cell may be obtained from the subject to be treated or from a different subject. The reference T cell may be a T cell from a healthy subject or from a subject having an autoimmune disease that has not yet been treated with one or more TNFR2 activators.

Examples of autoimmune diseases that can be treated using a pharmaceutical composition of the invention in a subject identified as likely to respond to treatment according to one or more of the diagnostic methods of the invention include type 1 diabetes, alopecia areata, ankylosing spondylitis, antiphospholipid syndrome, autoimmune Addison's disease, autoimmune hemolytic anemia, autoimmune hepatitis, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatricial pemphigoid, CREST syndrome, cold agglutinin disease, Crohn's disease, discoid lupus, systemic lupus erythmatosous, ulcerative colitis, psoriatic arthritis, essential mixed cryoglobulinemia, fibromyalgia-fibromyositis, Graves' disease, Guillain-Barré, Hashimoto's thyroiditis, hypothyroidism, idiopathic pulmonary fibrosis, idiopathic thrombocytopenia purpura (ITP), IgA nephropathy, juvenile arthritis, lichen planus, lupus, Meniere's disease, mixed connective tissue disease, multiple sclerosis, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, Stiff-Man syndrome, Devic's disease, Takayasu arteritis, temporal arteritis/giant cell arteritis, ulcerative colitis, uveitis, vasculitis, vitiligo, Wegener's granulomatosis, and an autoimmune neurological disorder. In particular, subjects having type 1 diabetes, celiac sprue-dermatitis, Crohn's disease, Graves' disease, hypothyroidism, lupus, multiple sclerosis, psoriasis, rheumatoid arthritis, sarcoidosis, Sjögren's syndrome, or ulcerative colitis, that are identified as likely to respond to therapy according to the diagnostic methods of the invention can be treated. An autoimmune neurological disorder may be an autoimmune-mediated disorder that causes damage to neurons, such as motoneurons. Particular autoimmune neurological disorders include autoimmune Alzheimer's disease, autoimmune Parkinson's disease, and autoimmune-mediated amyotrophic lateral sclerosis (ALS).

Substantially undetectable C-peptide levels in a sample (e.g., blood, a blood component (such as serum or plasma), or urine) from a subject having type 1 diabetes indicate that the subject as unlikely to respond to treatment with a pharmaceutical composition containing one or more TNFR2 activator (e.g., the subject may be excluded from such therapy or may be administered TNFR2 therapy in combination with a cellular therapy, such as a pluripotent cell (e.g., a Hox11+ cell)). Detectable C-peptide levels (e.g., levels greater than about 1.5 pmol/L) in a sample from a subject having type 1 diabetes indicate that the subject is likely to respond to the treatment with a pharmaceutical composition containing one or more TNFR2 activators. The subject may be a long term diabetic. The compositions of the invention may be used to treat the subject having type 1 diabetes and identified as likely to respond to the treatment with a TNFR2 activator according to any one or more of the methods of the invention.

In addition, a C-peptide to creatinine ratio of less than about 4 pmol/mmol in a urine sample from a subject having type 1 diabetes may also indicate that the subject is unlikely to respond to the treatment with a pharmaceutical composition containing one or more TNFR2 activator (e.g., the subject may be excluded from such therapy or may be administered TNFR2 therapy in combination with a cellular therapy, such as a pluripotent cell (e.g., a Hox11+ cell)). A C-peptide to creatinine ratio of greater than about 4 pmol/mmol in a urine sample from a subject having type 1 diabetes may indicate that a subject is likely to respond to the treatment with one or more TNFR2 activators. A C-peptide to creatinine ratio of from about 4 pmol/mmol to about 11 pmol/mmol in a urine sample from a subject having type 1 diabetes may indicate that a subject is likely to respond to the treatment with one or more TNFR2 activators. The C-peptide to creatinine ratios in urine samples can be determined as described in Besser et al., (*Diabetes Care* 34:607-609, 2011), which is incorporated herein by reference. Those subjects identified as being likely to respond to treatment with a TNFR2 activator (e.g., BCG) may subsequently be treated one or more times with a TNFR2 activator, such as BCG.

Pharmaceutical compositions of the invention may contain one or more TNFR2 activators include Bacillus Calmette-Guerin (BCG), complete Freund's adjuvant, TNF-α, a TNF-α receptor II agonist (non-limiting examples of TNFR2 agonists, such as antibodies, are described in U.S. Pat. Nos. 7,582,313, 8,017,392, and 8,173,129, which are incorporated herein by reference), a TNF-α mutein (non-limiting examples of TNF-α muteins are described in U.S. Pat. No. 5,597,899, which is incorporated herein by reference), interleukin-1, interleukin-2, tissue plasminogen factor, lipopolysaccharide (LPS), lymphotoxin, and cachectin. Some of the pharmaceutical compositions of the invention may be capable of inducing expression of TNF-α in a subject upon administration. Other compositions of the invention may specifically activate the TNF-α receptor II (as an agonist) and/or induce activation of the NF-κB pathway in an autoreactive immune cell (e.g., autoreactive CD8+ T cell) of the subject upon administration. Preferably, administration of the composition of the invention also causes death of one or more autoreactive immune cells in the subject. The compositions of the invention may also cause expansion of regulatory T cells (e.g., regulatory CD4+ T cell) in the subject. The compositions of the invention may also reduce or treat a complication from hyperglycemia (e.g., kidney damage, neurological damage, cardiovascular damage, damage to the retina, damage to the feet, damage to the legs, damage to the heart, or ketoacidosis) in a subject having type 1 diabetes.

A TNFR2-activator-containing pharmaceutical composition of the invention may be used to treat type 1 diabetes in a subject (e.g., a human) a second or subsequent time if, following a first treatment, HbA1c levels in a sample (e.g., blood, a blood component (such as serum or plasma), or urine) from the subject increase or remain the same relative to a reference HbA1c level from the subject prior to the previous treatment. A decrease in HbA1c levels in a treated subject may indicate that the subject is responding to the TNFR2 activator treatment (e.g., the subject may not need a second or subsequent treatment). HbA1c levels in a subject that decrease by at least about 0.1% (e.g., at least about 0.15%, at least about 0.2%, at least about 0.25%, at least about 0.3%, at least about 0.4%, at least about 0.5%, at least about 0.6%, at least about 0.7%, at least about 0.8%, at least about 0.9%, at least about 1.0%) within about 4 years (e.g., within about 3 years) after administration of a TNFR2 activator to the subject indicate the subject is responding to the treatment.

Cellular Therapies

The identification of a subject having type 1 diabetes with a substantially undetectable C-peptide level (e.g., a C-peptide level of less than about 1.5 pmol/L) according to the methods of the invention may indicate that the subject would benefit from, or is in need of, treatment with β-islet cells or cells capable of regenerating β-islet cells, such as pluripotent cells (e.g., Hox11+ splenocytes). Hox11+ splenocytes are an endogenous source of cells that can regenerate β-islet cells in a subject in vivo, as is described in International Pub. No. WO 2005/042727, which is incorporated herein by reference. Therefore, a subject having type 1 diabetes may have a long term benefit (e.g., within 4 years, such as within 3 years) from cellular treatment if the treatment with one or more TNFR2 activators kills autoreactive T cells and allows the subject to regenerate endogenous β-islet cells (e.g., through expansion of endogenous β-islet cells or due to differentiation of pluripotent cells, such as Hox11+ splenocytes, into β-islet cells). Other types of pluripotent cells that can differentiate into β-islet cells in a subject may be administered to the subject, including, for example, those described in U.S. Pat. Nos. 7,432,104 and 8,008,075, which are incorporated herein by reference. Substantially undetectable C-peptide levels (e.g., less than about 1.5 pmol/L) in a sample from a subject having type 1 diabetes may indicate that the subject has lost the ability to regenerate β-islet cells from, e.g., the Hox11+ splenocyte compartment. Thus, the subject may benefit from administration of an exogenous source of β-islet cells.

Non-limiting examples of pluripotent cells that may be administered to a subject in need thereof according to the present invention include those described in, e.g., WO 2002/059278, WO 2003/026584, WO 2005/042727, WO 2006/074308, WO 2012/152717, U.S. Pat. Nos. 7,432,104, and 8,008,075, which are incorporated herein by reference. Compositions containing one or more pluripotent cells (e.g., Hox11+ splenocytes) may be administered prior to, subsequent to, or concurrently with the TNFR2 activator-containing compositions, or the two compositions may be combined for administration in a single dosage form.

Formulations of the Pharmaceutical Compositions of the Invention

The pharmaceutical compositions of the invention containing one or more TNFR2 activators may be formulated for administration by any route, e.g., intradermal, intramuscular, parenteral, intravenous, intra-arterial, intracranial, subcutaneous, intraorbital, intraventricular, intraspinal, intraperitoneal, or intranasal. The composition of the invention may be formulated for intradermal administration.

The pharmaceutical composition of the invention may contain a pharmaceutically acceptable carrier or excipient. Such carriers or excipients may be selected from, for example, water, phosphate-buffered saline (PBS), acetate-buffered saline (ABS), Ringer's solution, dextrose, glycerol, ethanol, or the like and combinations thereof. In addition, if desired, a composition for administration to a subject can contain minor amounts of auxiliary substances, such as wetting or emulsifying agents, or pH buffering agents that enhance the effectiveness of the composition.

Also, TNFR2 activators may be administered at multiple different times and/or frequencies. For example, one or more (e.g., 1, 2, 3, 4, or 5, or more) doses of TNFR2 activators may be administered daily, weekly, monthly, or yearly (e.g., twice daily, biweekly, quarterly, bi-annually, or tri-annually).

A TNFR2-activator-containing composition of the invention (e.g., BCG) may be administered one or more times (e.g., two or more times, such as twice) to a subject having type 1 diabetes and identified, according to the diagnostic methods described herein, as likely to respond to treatment with the TNFR2 activator. The TNFR2-activator-containing composition may be administered two or more times, spaced by, e.g., about 1 week (e.g., about 2 weeks, about 3 weeks, about 4 weeks, about 5 weeks, about 6 weeks, about 7 weeks, or about 8 weeks or more) between administrations. In some embodiments, administration of the TNFR2 activator composition may be spaced at least two weeks apart (e.g., four weeks apart).

The TNFR2 activator may be a TNF-α inducing substance, such as BCG. The pharmaceutical composition may contain greater than $2\times10^6$ CFU/dose of BCG (e.g., greater than $2.3\times10^6$ CFU/dose of BCG). The composition may contain less than $4\times10^6$ CFU/dose of BCG. The composition may contain from about $2\times10^6$ to about $2.5\times10^6$, from about $2.5\times10^6$ to about $3\times10^6$ CFU/dose of BCG, from about $3\times10^6$ to about $3.5\times10^6$ CFU/dose of BCG, or from about $3.5\times10^6$ to about $4\times10^6$ CFU/dose of BCG. The composition may contain from about $2\times10^6$ to about $4\times10^6$ CFU/dose of BCG. The composition of may contain from about $2.3\times10^6$ to about $4\times10^6$ CFU/dose of BCG. The composition may contain from about $2.5\times10^6$ to about $4\times10^6$ CFU/dose of BCG. In an embodiment, the BCG composition may be lyophilized. Alternatively, the compositions may contain a saline solution of BCG. The saline solution of BCG may be made by reconstituting lyophilized BCG in saline solution. The solution may have a volume of less than about 0.2 cc per dose (e.g., about 0.1 cc per dose).

A composition of the invention containing one or more pluripotent cells may be administered after the subject is identified as being unlikely to respond to treatment with a TNFR2 activator. The compositions containing pluripotent cells administered to a subject in need thereof may be formulated for administration by any route, e.g., intradermal, intramuscular, parenteral, intravenous, intra-arterial, intracranial, subcutaneous, intraorbital, intraventricular, intraspinal, intraperitoneal, or intranasal. Preferably, the composition containing one or more pluripotent cells is administered parenterally, such as through injection (e.g., intravenous or intramuscular) or surgical transplantation. The compositions containing pluripotent cells may be administered to a subject in need thereof one or more times (e.g., 1, 2, 3, 4, or 5, or more). The one or more administrations may be spaced by a week, 2 weeks, 3 weeks, 4 weeks, 5 weeks, 6 weeks, 2 months, 6 months, 1 year, 1.5 years, 2 years, or 3 years or more. Administration of a TNFR2 activator may be performed a week, 2 weeks, 3 weeks, 4 weeks, 5 weeks, 6 weeks, 2 months, 6 months, 1 year, 1.5 years, 2 years, or 3 years or more after administration of a composition containing pluripotent cells. Alternatively, the TNFR2 activator may be administered concurrently with, or subsequently to, administration of a composition containing pluripotent cells by any route described above (e.g., the routed may be the same or different), or the compositions may be combined for administration in a single dosage form.

Kits of the Invention

Kits for CD8 Surface Protein Assay

The invention provides kits including a container for a sample from a subject, a preservative (e.g., dasatinib, such as a sufficient quantity to produce an at least about 10 nM (e.g., at least about 50 nM, at least about 100 nM, at least about 200 nM, at least about 500 nM, or at least about 1 μM) final solution of dasatinib in a sample; e.g., a 1 mL solution having at least about 10 mM dasatinib or a container with at least about 1.0 μg to about 25 mg of dasatinib in solid form), instruments for collecting the sample and/or placing the sample in the container, and instructions for collecting and preserving the sample. The kit may further contain a CD8 antibody conjugated to a fluorochrome and/or a TNFR2 activator (e.g., Bacillus Calmette-Guérin (BCG), complete Freund's adjuvant, TNF-α, a TNF-α receptor II agonist, a TNF-α mutein, interleukin-1, interleukin-2, tissue plasminogen factor, lipopolysaccharide (LPS), lymphotoxin, or cachectin). The instructions in the kits described above may also explain how a practitioner (e.g., a physician, a nurse, or a laboratory assistant) may use the sample from the subject to determine whether the subject is likely to respond to treatment with a TNFR2 activator or not. The kits may further contain an implement for collection and transfer of the sample into the container (e.g., a needle or a catheter), components for keeping the cells at a defined temperature (e.g., between about 4° C. and about 27° C.), such as a coolant (e.g., an ice pack, dry ice, cooling pouch, or cooling plates). The kit may also include a cold box or insulated carrier for transport of the cell sample, if necessary.

Kits for C-Peptide Detection

The invention also provides kits including a device having a capture agent (e.g., an antibody that binds C-peptide) immobilized on its surface, a detecting binding agent conjugated to a peroxidase enzyme (e.g., an antibody that binds C-peptide selectively), a peroxidase substrate, and instructions explaining how a practitioner (e.g., a physician, a nurse, or a laboratory assistant) may use the contents of the kit for analysis of a sample from a subject to determine whether the subject is likely to respond to treatment with a TNFR2 activator or not.

Kits for HbA1c Assay The invention also provides kits including a container for storing a sample from a subject and instructions for determining HbA1c levels in the sample and using the HbA1c levels to determine if the subject requires administration of a TNFR2-activator-containing composition or not.

The following examples are meant to illustrate the invention. They are not meant to limit the invention in any way.

EXAMPLES

Example 1. Identification of Subjects Having Type 1 Diabetes as Likely to Respond to Treatment with a TNFR2 Activator Prior to treatment with a pharmaceutical composition of the invention (e.g., a TNFR2 activator), a subject (e.g., human) may be tested to determine whether the subject is likely to respond to the treatment. The test may be performed using a sample (e.g., blood, a blood component, or urine) collected from the subject. For example, to prepare a serum sample, blood may be collected by venipuncture, allowed to clot, and serum may be separated by centrifugation. To prepare a plasma sample, blood may be collected by venipuncture into tubes containing heparin or EDTA as anticoagulant; a plasma fraction may then be separated from the samples. To prepare a urine sample, a 24 hour urine sample (without preservative) may be collected. Cellular debris may be removed from the sample prior to testing by either filtration or centrifugation.

The prepared sample from the subject may then be assayed using, e.g., a Mercodia ULTRASENSITIVE™ C-peptide ELISA kit (manufactured by Mercodia AB, Uppsala, Sweden) to give C-peptide levels in the sample from the subject. The subject is identified as being unlikely to respond to the treatment with a TNFR2 activator if the measured C-peptide levels are lower than about 1.5 pmol/L. A subject identified as having a substantially undetectable C-peptide level may be excluded from treatment with a TNFR2-activator-containing composition. In particular, such a subject may be determined as having an insufficient number of endogenous β-islet cells remaining or an insufficient amount of pluripotent cells, such as Hox11+ splenocytes, remaining to differentiate into β-islet cells, and therefore unlikely to exhibit a restoration of, or improvement in, normoglycemia following therapy with a TNFR2 activator. The determination that a subject has a substantially undetectable C-peptide level may also indicate that the subject would benefit from transplantation of β-islet cells or pluripotent cells, such as Hox11+ splenocytes, that can differentiate into β-islet cells. The subject may be determined as likely to respond to treatment with a TNFR2 activator if the measured C-peptide levels are greater than about 1.5 pmol/L; this subject may be treated with a TNFR2 activator composition of the invention with an expectation that such therapy will result in regeneration of β-islet cells and/or restoration of, or improvement in, normoglycemia.

The test may be repeated one or more times to correct for possible single measurement variability of data.

Example 2. Treatment of Type 1 Diabetes in a Human with a Pharmaceutical Composition of the Invention Prior to treatment with a TNFR2 activator (e.g., BCG), a sample (e.g., blood) may be taken from the subject identified in Example 1 as likely to respond to the treatment. The sample may be analyzed for HbA1c levels to determine the baseline HbA1c level for the study.

A pharmaceutical composition containing BCG reconstituted in saline may be administered to the subject as two intradermal injections four weeks apart in a dose containing 1.0-2.3×10⁶ CFU/administration (volume=0.1 cc/administration). After the treatment, the subject may be monitored over time by testing samples obtained from the subject using functional assays (autoreactive CD8+ T cell assay and regulatory CD4+ T cell assay), which are described further below.

After the treatment, 1 year (e.g., 2 years, 3, years, 4, years, 5 years, or 6 years) after administration of the TNFR2 activator, such as BCG, a sample from the subject may be assessed for HbA1c levels to determine the endpoint and to confirm the long-term success of the treatment. A decrease of at least about 0.1% (e.g., 0.15%, 0.2%, 0.25%, 0.3%, 0.4%, or 0.5%) in HbA1c levels relative to the baseline HbA1c level would be indicative of a long-term success of the treatment.

The subject may be continued to be monitored for changes in HbA1c levels. An increase of at least about 0.1% (e.g., 0.2%, 0.3%, 0.4%, or 0.5%) in HbA1c levels over the baseline HbA1c level may indicate that the subject should be administered the pharmaceutical composition of the invention again.

Immune Monitoring

1. T Cell Assays

CD4+ and CD8+ T cells can be isolated from fresh human blood within 1.5 h of venipuncture using Dynal CD4 positive isolation kit and Dynal CD8 positive isolation kit (Invitrogen, Carlsbad, CA). This method is unique in yielding cells that are both free of magnetic particles and free of the positive selection with the antibody.

2. Detection of Autoreactive CD8+ T Cells in Type 1 Diabetes

Highly purified, viable and high yield CD8+ T cells can be utilized for tetramer staining, as previously described (Verginis et al., *Proc. Natl. Acad. Sci. U.S.A.* 105:3479-3484, 2008). Tetramers are diagnostic reagents that are composed of the binding region of specific HLA class 1 proteins with loaded peptides in the exterior binding groves. The tetramers are then made fluorescent and act as diagnostic reagents that can bind to T cells with specific reactivity to the presented peptide fragment. For detection of autoreactive T cells to insulin, tetramers to HLA *0210 insulin beta 10-18 with a fragment of HLVEALYLV (SEQ ID NO: 1; Beckman Coulter #T02001) can be used. For negative control tetramers, the following tetramer reagents can be used: HLA *0201 Her-2/neu with a sequence to KIFGSLAFL (SEQ ID NO: 2; Beckman Coulter #T02001), a breast cancer peptide, HLA *0201 null without a non-specific peptide fragment (Beckman Coulter #T01010) and/or a tetramer to the CMV virus HLA-A *0201 CMGPP65 with a sequence of NLVPMVATV (SEQ ID NO: 3; Beckman Coulter #T01009).

Tetramer reagent staining can be conducted both after 12 h of culture at 26° C. followed by 6 h at 37° C. and/or after 1 h rest at 26° C. followed by 12 h at 37° C. The cells can be then stained with Sytox-green (MBL International Co., Woburn, MA) and/or CD8 antibodies (BD Biosciences, San Jose, CA). All cells can be stained at 4° C. in the dark for 30 minutes and then can be washed twice in Hank's buffer with 2% heat-inactivated bovine serum. On average, 100,000 highly pure CD8+ T cells can be analyzed to ensure clear data points and to allow for the detection of the rare autoreactive T cells. All cells can be fresh to prevent fixation artifacts and to allow for the quantification of dead versus viable cells. Cell viability can be quantified by either of two stains that fluorescently label dead cells, Sytox (MBL International Co., Woburn, MA) or propidium iodide (PI).

3. Detection of $T_{reg}$ CD4+ Cells in Type 1 Diabetics

Two different methods can be used for the detection of $T_{REG}$ cells. $T_{REG}$ cells can be detected using CD4, $CD25^{bright}$, and Foxp3 staining or with CD4, $CD25^{bright}$, and $CD127^{low}$ antibody staining. Briefly, isolated CD4 positive cells can be incubated with CD4-PE-Cy5 (clone RPA-T4) and CD25-PE (clone BC96) antibodies for 20 minutes at room temperature. After washing, cells can be fixed with Foxp3 Fix/Perm solution (Biolegend) for 20 minutes at room temperature. Cells can be washed and permeabilized with Biolegend's Foxp3 Perm Buffer for 15 minutes at room temperature. Cells can be then stained with Foxp3 Alexa Fluor477 antibody (clone 259D) for 30 minutes. Isotype controls can be done for each sample prior to flow cytometric analysis. Alternatively, for detection of T regulatory cells, staining can also be performed with a CD4 antibody (clone RPA-T4, BD Biosciences, San Jose, CA) and an anti-human CD127 antibody (clone hIL-7R-M21, BD Biosciences).

Other methods for detecting $T_{REG}$ cells are described in U.S. Ser. No. 61/763,217, which is incorporated herein by reference in its entirety.

Example 3. Detection of CD8$^+$ T Cells in a Sample from a Subject Having EBV Infection Materials and Methods Subjects Patients having type 1 diabetes were recruited at the Massachusetts General Hospital. The diabetic patients were routinely screened to characterize the course of disease and to exclude subjects with potentially interfering medical conditions. During screening, three patients were identified as having long-term type 1 diabetes and recent onset of EBV. Diabetics without EBV infection (N=66) were used in this study as a reference population. All patient and control blood was drawn into BD VACUTAINER™ tubes (BD, Franklin Lakes, NJ) containing EDTA.

Ethics Statement

The study was approved by the Massachusetts General Hospital Institutional Review Board (IRB Protocol No. 2001P-001379). Written consent was obtained from all blood donors.

Detection of Epitope-Specific CD8$^+$ T-Cells

For the detection of specific subpopulations of T-cells with restricted antigen specificity, commercially available HLA Class I reagents loaded with small peptide fragments were utilized. These commercial reagents are commonly referred to as Tetramers (MBL International, DesPlaines IL., formerly Beckman Coulter, Fullerton, CA) or Dextramers (Immudex, Fairfax, VA). The two T-cell detection methods differ in the backbone structures of the detecting reagent but not in the binding specificity to autoreactive T-cells. Tetramer or dextramer reagents are purchased fluorescently labeled for detection of the bound reagent to antigen specific T-cell with a flow cytometer.

For the studies contained in this paper, two types of antigen-specific T-cells were detected, i.e., EBV-specific T-cells (HLA class I loaded peptide; GLCTLVAML (SEQ ID NO: 4)) or insulin-B autoreactive T-cells (HLA class I loaded Insulin-B chain; HLVEALYLV (SEQ ID NO: 1)). For background fluorescence of T-cells a matched HLA class I structure was loaded with an irrelevant peptide (Beckman Coulter, Immudex).

Isolated CD8$^+$ T-Cell Method

For the direct isolation of CD8$^+$ T-cells from fresh blood a "Detach-a-bead" CD8 positive isolation kit based on paramagnetic beads coated with anti-CD8 antibody was used (Life Technologies, Carlsbad, CA) (see Burger et al., PLOS One, 6: e22430, 2011, which is incorporated herein by reference). The beads were allowed to attach for 1 hr at room temperature under continuous agitation on a tumbler. The bead/cell complexes were then immobilized using a magnet and any unbound (non-CD8) cells removed by repeated washing with HBSS (Hank's Balanced Salt Solution without calcium and magnesium, Invitrogen, Grand Island, NY) containing 2% FBS (fetal bovine serum). The beads were then detached from the remaining CD8$^+$ cells using a Detach-A-Bead reagent supplied in the isolation kit. This reagent is a polyclonal antibody directed against the antigen recognition site of the CD8 antibody coated on the beads. It detaches the antibody/bead complex from the cells by means of competition for the CD8 antibody binding site, essentially leaving a virgin cell.

Isolated CD8$^+$ T-cells were then labeled with PE (phycoerythrin) labeled tetramers or dextramers (20 min, RT (room temperature), in the dark) and subsequently with APC-anti-CD8 antibodies (10 minutes at RT in the dark; clone SK1, BD Biosciences, San Jose, CA) to determine purity of the isolated cell preps. The samples were then fixed with HBSS 0.1% formaldehyde buffer, washed with HBSS, and resuspended in HBSS/0.05% formaldehyde for flow cytometry.

Whole Blood Method

Blood samples were first washed with 50 volumes of HBSS containing 2% FBS. They were then labeled with the tetramers or dextramers (20 min at RT in the dark) and subsequently with APC-anti-CD8 antibodies (10 minutes at RT in the dark) to enable gating on CD8$^+$ T-cells. The samples were then simultaneously lysed and fixed with $NH_4Cl$/formaldehyde buffer, washed with HBSS, and resuspended in HBSS/formaldehyde for flow cytometry.

Flow Cytometry

Cells were analyzed using a FACSCalibur flow cytometer (BD Biosciences, San Jose, CA) and data collected in list mode. Data analysis was performed using Cell Quest software (BD Biosciences). Flow gates were set "open" for inclusion of all cells. The open gate included cells of all sizes, but excluded cell debris, red blood cells, fragmented cells, and apoptotic bodies. PE and APC fluorescence were detected in FL2 and FL7, respectively. The percentage CD8$^+$ T-cells was defined as the ratio of the number of CD8 positive events and the total number of events in the lymphocyte gate.

ELISA

C-peptide was determined by ELISA in blood serum of the EBV-infected patients. The ULTRASENSITIVE™ C-peptide ELISA was from Mercodia (Uppsala, Sweden). The kit was used according to the manufacturers' instructions. Serum levels of VCA IgM, Early Antigen D, and EBNA were determined by Massachusetts General Hospital Clinical Laboratory Services.

Statistics

Figure 2:
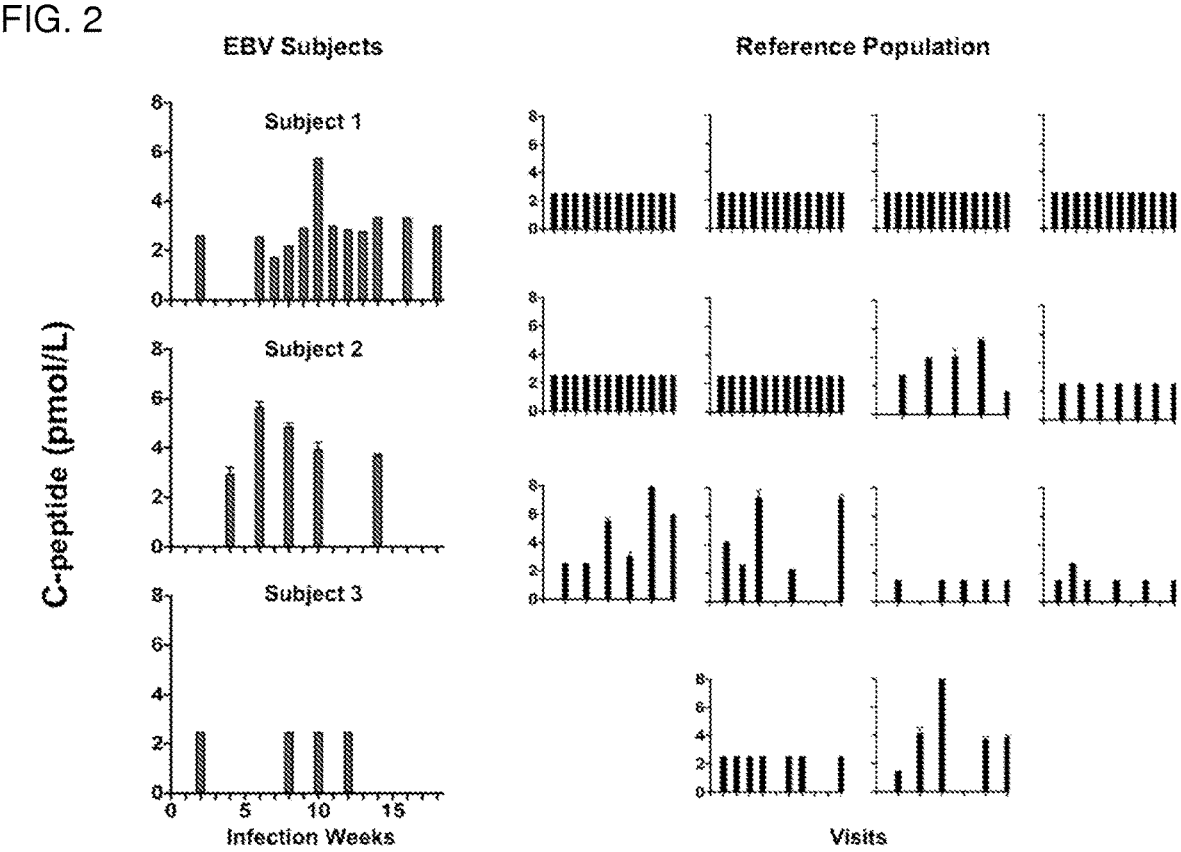
FIG. 2 is a set of several graphs showing the time course of C-peptide levels in each of three EBV-infected subjects versus a reference population of subjects having type 1 diabetes without active EBV infection. Subjects 1 and 2 showed a transient increase in C-peptide that was statistically significant as compared to the reference population ($p<0.04$ and $p=0.00134$, respectively). Subject 3 did not show increased C-peptide levels.

Statistical significance was determined using the unpaired, one-tailed Student's t-test at a confidence level of 0.05 (FIGS. 3A and 2B) or a one sided Kolmogorov-Smirnov test (FIG. 2).

Results

Clinical Profiles

In the course of routine visits of type 1 diabetes patients, three patients with recent onset EBV infection were identified, also known clinically as mononucleosis or "mono" (see Table 1). These patients were followed closely for at least 15 weeks after presentation. Recent onset EBV infection offers an opportunity to study the prevalence and traits of autoimmune and EBV-specific T-cells both during and after clinical symptoms of EBV infection. It also offers the opportunity to document the reproducibility of the past observation in a clinical trial of BCG treatment that EBV infection caused a transient increase in insulin production by the pancreas, measured as co-secreted C-peptide (see Faustman et al., PLOS One, 7: e41756, 2012, which is incorporated herein by reference).

TABLE 1

A Summary of Clinical Characteristics for the Three EBV Subjects.
Clinical characteristics of subjects

|  | Sex | Age (y) | Age at Onset (y) | T1D Duration (y) | HbA1c (%) | GADA Status |
|---|---|---|---|---|---|---|
| Subject 1 | M | 47 | 17 | 30 | 6.2 | Pos. |
| Subject 2 | F | 17 | 11 | 6 | 8.0 | Pos. |
| Subject 3 | F | 21 | 2 | 19 | 9.6 | Neg. |

The EBV infections were first clinically diagnosed by standard serologic methods and symptoms. The clinical characteristics of these subjects are summarized in Table 1. All subjects had established type 1 diabetes, with durations of 6, 19, and 30 years and elevated HbA1c. Two of the subjects (Subjects 1 and 2) were positive for glutamic acid decarboxylase GAD65 autoantibody, which is an islet-specific marker for type 1 diabetes.

Time Course of EBV Infection

After presenting with symptoms and a clinical diagnosis of EBV infection, a more detailed EBV antibody serology was performed to determine the details of the time course of the infection and to estimate the time of onset of the infection relative to the sequential blood studies performed here (Table 2).

TABLE 2

Results for EBV antibody testing on blood samples drawn during the first visit for the three EBV subjects and correlation with estimated start of EBV infection.
EBV antibody results

|  | 0-6 Weeks, VGA IgM | 4-8 Weeks, Early Antigen D | 6-8 Weeks Sustained, EBNA | Estimated Duration |
|---|---|---|---|---|
| Subject 1 | Negative | Positive | n/a | 2 weeks |
| Subject 2 | Positive | Positive | Negative | 4 weeks |
| Subject 3 | Positive | Negative | Negative | 2 weeks |

Subclasses of EBV antibodies to different parts of the EBV viral particle peak at different times after infection were detected. A combination of VCA IgM, Early Antigen D, and EBNA was used. These markers peak at 0-6 weeks, 4-8 weeks, and 6-8 weeks after EBV infection, respectively (Table 2). All subsequent data reported in this study, especially timelines of immunologic events, were plotted and extrapolated to an infection date of "0". For Subject 1, the presentation time for the present study was estimated to be week 2 after infection. For Subject 2, the presentation time was estimated to be week 4 after infection. For Subject 3, the presentation time was estimated to be week 2 after infection.

Detection of EBV-Specific CD8+ T-Cells

Figure 1B:
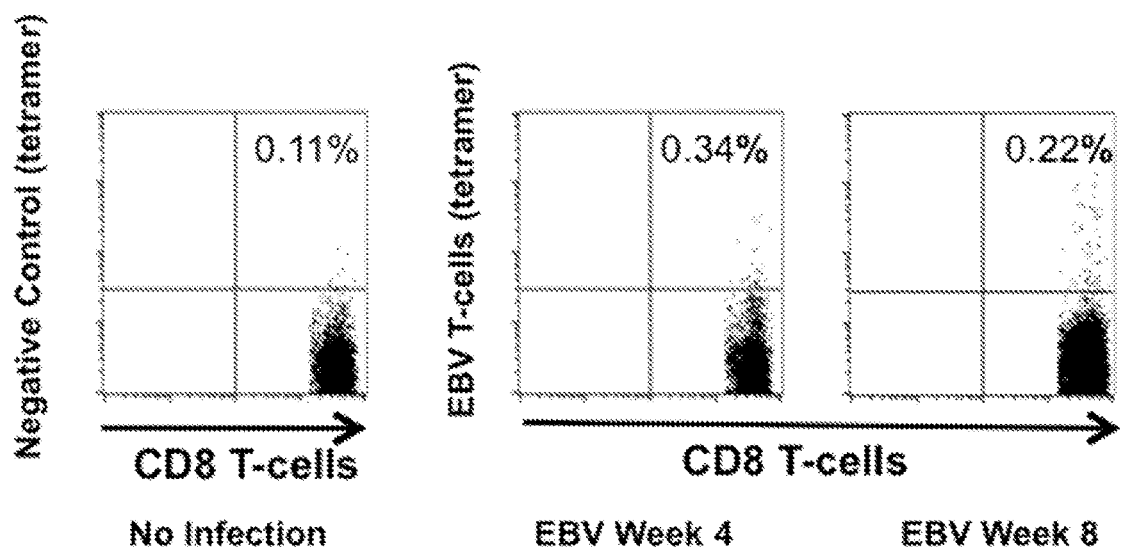
FIG. 1B is a set of three dot plots of flow cytometry results of analyses of tetramer-stained samples containing EBV-specific autoreactive $CD8^+$ T cells and the negative control. The level of non-specific tetramer binding by $CD8^+$ T-cells was determined using a tetramer loaded with an irrelevant peptide sequence (Negative Control, left panel). The middle and right panels show examples of positive staining using EBV-specific tetramers.

Although the typical clinical method of diagnosing EBV infections involves antibody testing, it is possible in a research setting to confirm infection by direct monitoring of newly created EBV-specific T-cells. EBV-specific tetramers were used, i.e., HLA class I proteins loaded with a synthetic peptide sequence GLCTLVAML (SEQ ID NO: 4). Thus, EBV-specific CD8+ T-cells were detected using flow cytometry (FIGS. 1A and 1B). Although a slightly different method for detection of these EBV-specific T-cells was utilized in Subject 1, versus Subjects 2 and 3 (isolated CD8+ T-cells versus direct observations of CD8+ T-cells in lysed blood), all subjects had an early rise in EBV-specific T-cells above background levels of fluorescence (FIG. 1B).

Time Course of C-Peptide in EBV-Infected Subjects

Research over the last fifteen years has shown that a systemic increase of TNF, or induction of TNF with either BCG or EBV, results in pancreas regeneration with the recovery of C-peptide (see Kodama et al., Science, 302: 1223-1227, 2003; Faustman et al., PLOS One, 7: e41756, 2012; and Faustman, J. Clin. Immunol. 13:1-7, 1993, which are incorporated herein by reference). C-peptide is the protein co-secreted with insulin and a sensitive method to measure insulin secretion from the pancreas in the presence of exogenously administered insulin.

To determine the impact of EBV infections on insulin secretory capacity, serial serum C-peptide levels were monitored for at least 15 weeks after the subjects with EBV presented to the research clinic. A simultaneously studied reference population of non-EBV infected long-term diabetics was similarly monitored for 15 weeks. The monitoring of the reference subjects for fasting morning C-peptide demonstrated the subject and assay variability.

C-peptide in EBV-infected Subjects 1 and 2 showed a statistically significant increase of p=0.04 and p=0.0013 over that in the reference population, respectively. Subject 3 showed no significant increase in pancreatic C-peptide (FIG. 2).

Impact of EBV on Insulin-B Autoreactive T Cells in Type 1 Diabetics

Previous data show that treatment of NOD mice or diabetic humans with BCG (or the non-cGMP equivalent Complete Freund's Adjuvant (CFA)) results in a transient increase in dead autoreactive T-cells. In the NOD mouse, pancreas-residing autoreactive T-cells are observed to undergo apoptosis directly on top of the insulin-secreting islets in the pancreas with TNF, BCG or CFA (see Kuhtreiber et al., J. Mol. Endocrinol. 31:373-399, 2003, which is incorporated herein by reference). In humans, the impact of TNF on autoreactive T-cells can be monitored by the rapid release of dead autoreactive T-cells into the circulation (see Faustman et al., PLOS One, 7: e41756, 2012, which is incorporated herein by reference). Increased TNF or TNFR2 agonistic antibodies are known to cause apoptosis of murine and human diabetic autoreactive T-cells in culture (see Ban et al., Proc. Nat. Acad. Sci. USA, 105:13644-13649, 2008, which is incorporated herein by reference).

Figure 3A:
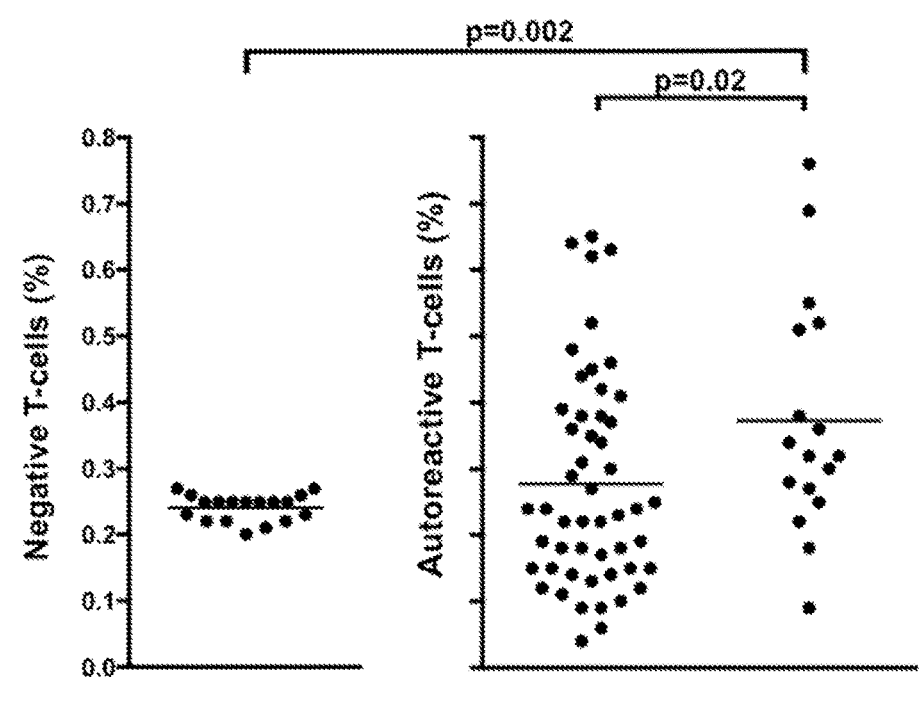
FIG. 3A is a set of graphs quantifying the presence of insulin-B autoreactive T cells and demonstrating an increased presence of circulating insulin-B autoreactive T-cells after EBV infection in type 1 diabetes as compared to the levels of autoreactive T-cells in an uninfected type 1 diabetes subjects. Background fluorescence for peripheral T-cells from the same subjects stained with an irrelevant peptide bearing class I reagent was 0.2%.

To determine whether EBV infection similarly kills or injures autoreactive T-cells, insulin-B autoreactive CD8+ T-cells in the peripheral blood of the three recently EBV-infected subjects were detected and compared to uninfected long-term diabetic subjects. Tracking of insulin-B autoreactive T-cells in long-term diabetics is feasible. With sensitive monitoring methods about 41% (21 out of 51) of randomly recruited long-term type 1 subjects had detectable insulin-B autoreactive T-cells (0.28% to 0.65%, FIG. 3A). The same type 1 diabetic CD8+ T-cells stained with negative dextramer reagents exhibited a background signal range of 0.19% to 0.27% (FIG. 3A).

As previously shown for long-term diabetics exposed to TNF inducing infections, the EBV infected subjects exhibited an overabundance of insulin-B autoreactive T-cells in peripheral blood after infection. The mean percentage of insulin-B autoreactive T-cells in EBV-infected subjects was greater than that in the negative background staining (p=0.002), as well as in a matched population of uninfected reference diabetics (p=0.02). This finding supports the conclusion that infections that boost TNF result in the release of these autoreactive T-cells into the circulation.

Newly Released Insulin-B Autoreactive T-Cells have Abnormally Low CD8+ Density

Figure 3B:
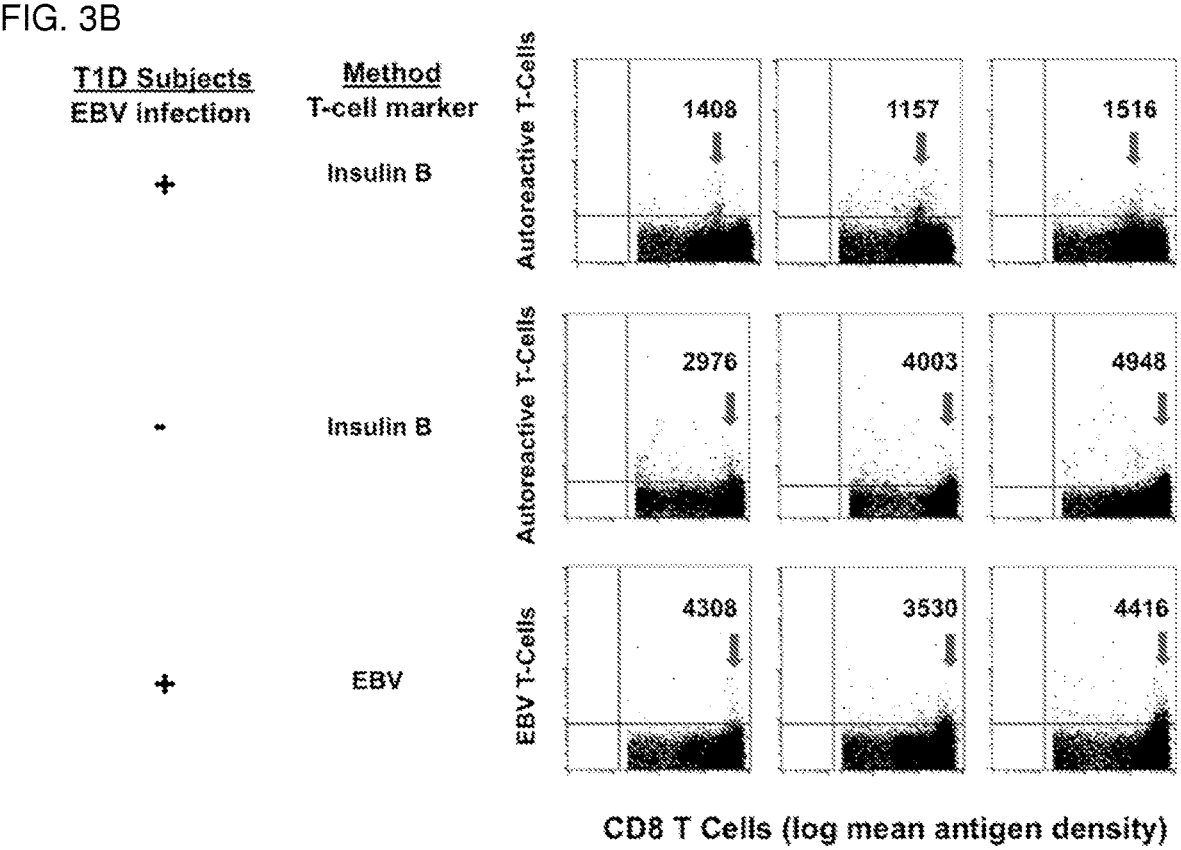
FIG. 3B is a set of flow cytometry histograms for samples from subjects having type 1 diabetes with or without EBV infection and quantifying CD8 protein density on the surface of T cells. Reductions in CD8 protein density on the surface of T cells were specific for the newly appearing insulin-B autoreactive T-cells of the EBV-infected subjects. Long-term type 1 diabetics without EBV infection had smaller numbers of peripheral insulin-B autoreactive T-cells, but the density of the CD8 protein on the surface of T cells was in the normal range. Also the EBV-specific T-cells from the EBV-infected subjects also had a normal density of CD8 protein.

A further analysis of the insulin-B autoreactive T-cells in long-term diabetics infected with EBV virus revealed some additional distinctive features of the antigen-specific CD8+ T-cells (FIG. 3B). Not only were there more insulin-B autoreactive CD8+ T-cells in the circulation after EBV infection, but also the density of the CD8 marker on the cells was dramatically lower. As shown in FIG. 3B, in three characteristic histograms, the CD8 mean log fluorescent density was 1408, 1157 and 1516 for the insulin-B autoreactive T-cells in EBV-infected subjects. In contrast, for insulin-B autoreactive T-cells from uninfected long-term diabetic subjects, the mean log antigen density of the CD8 marker was 2976, 4003, and 4948. The lower density of CD8 proteins in the EBV-infected subjects was not a generalized trend for all antigen-specific T-cells but specific for only the autoreactive T-cells. For these same infected subjects the log CD8+ T-cell density was normal for the EBV-specific T-cells. The CD8 protein density on the cell surface was 4308, 3530 and 4416, values that are similar to the density of the CD8 proteins on insulin-B autoreactive T-cells of uninfected diabetics (FIG. 3B). Loss of CD8+ marker is indicative of cellular damage or apoptosis of T-cells (see Diaz et al., *J. Leukoc. Biol.*, 76:609-615, 2004, which is incorporated herein by reference). Thus, the loss of the CD8 protein on the surface of autoreactive T cells in response to a TNFR2 activator, such as TNF-α or BCG, can be used as a proxy to diagnose the likelihood a subject with an autoimmune disease can be treated using a TNFR2 activator.

OTHER EMBODIMENTS

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are within the following claims.

The invention claimed is:

1. A method of treating a human subject that has type 1 diabetes, is receiving periodic insulin injection therapy, and has a C-peptide level in blood of from about 1.5 pmol/L to about 4.0 pmol/L, the method comprising
administering at least two doses of Bacillus Calmette-Guérin (BCG) to the subject, wherein each said dose is administered to the subject at least three years apart.

2. The method of claim 1, wherein, prior to administration of the BCG, the method further comprises contacting a blood sample from the subject with a device capable of detecting C-peptide in the blood sample.

3. The method of claim 1 further comprising measuring a reference HbA1c level in a blood sample from said subject prior to administration of the BCG to the subject.

4. The method of claim 2, wherein said device comprises an immobilized capture agent on the surface thereof that binds said C-peptide in said sample.

5. The method of claim 1, wherein the BCG is administered intradermally to the subject.

6. The method of claim 1, wherein the C-peptide level is determined when the subject is in a fasting state.

7. The method of claim 1, wherein the C-peptide level is determined when the subject is stimulated by administration of glucagon.

8. The method of claim 1, wherein said dose comprises an amount in a range of about $2\times10^6$ CFU to about $4\times10^6$ CFU of BCG.

* * * * *